(12) United States Patent
Cui et al.

(10) Patent No.: US 12,029,832 B2
(45) Date of Patent: Jul. 9, 2024

(54) THREE-DIMENSIONAL BIOPRINTING OF CARDIAC PATCH WITH ANISOTROPIC AND PERFUSABLE ARCHITECTURE

(71) Applicants: THE GEORGE WASHINGTON UNIVERSITY, Washington, DC (US); THE UNITED STATES OF AMERICA, AS REPRESENTED BY THE SECRETARY, DEPARTMENT OF HEALTH AND HUMAN SERVICES, Bethesda, MD (US)

(72) Inventors: Haitao Cui, Arlington, VA (US); Lijie Grace Zhang, Ashburn, VA (US); Yimin Huang, Beijing (CN)

(73) Assignee: The George Washington University, Washington, DC (US)

( * ) Notice: Subject to any disclaimer, the term of this patent is extended or adjusted under 35 U.S.C. 154(b) by 856 days.

(21) Appl. No.: 16/845,329

(22) Filed: Apr. 10, 2020

(65) Prior Publication Data

US 2020/0316254 A1 Oct. 8, 2020

Related U.S. Application Data

(63) Continuation of application No. PCT/US2018/055707, filed on Oct. 12, 2018.

(60) Provisional application No. 62/571,684, filed on Oct. 12, 2017.

(51) Int. Cl.
| | |
|---|---|
| A61L 27/38 | (2006.01) |
| A61L 27/26 | (2006.01) |
| A61L 27/36 | (2006.01) |
| B29C 64/106 | (2017.01) |
| B29C 64/124 | (2017.01) |
| B33Y 10/00 | (2015.01) |
| B33Y 70/00 | (2020.01) |
| B33Y 80/00 | (2015.01) |
| B29K 33/00 | (2006.01) |
| B29K 105/00 | (2006.01) |
| B29L 31/00 | (2006.01) |

(52) U.S. Cl.
CPC .......... *A61L 27/3625* (2013.01); *A61L 27/26* (2013.01); *A61L 27/367* (2013.01); *A61L 27/3808* (2013.01); *A61L 27/3826* (2013.01); *A61L 27/3834* (2013.01); *A61L 27/3873* (2013.01); *B29C 64/106* (2017.08); *B29C 64/124* (2017.08); *B33Y 10/00* (2014.12); *B33Y 70/00* (2014.12); *B33Y 80/00* (2014.12); *A61L 2430/20* (2013.01); *B29K 2033/08* (2013.01); *B29K 2089/00* (2013.01); *B29K 2105/0088* (2013.01); *B29L 2031/7546* (2013.01)

(58) Field of Classification Search
CPC ...... A61L 27/38; A61L 27/3804; A61L 27/40; A61F 2002/30985
See application file for complete search history.

(56) References Cited

U.S. PATENT DOCUMENTS

| | | | |
|---|---|---|---|
| 10,039,859 B2* | 8/2018 | Phopase | C08J 3/075 |
| 2005/0123581 A1* | 6/2005 | Ringeisen | A61P 19/00 |
| | | | 264/172.11 |
| 2008/0009830 A1 | 1/2008 | Fujimoto et al. | |
| 2013/0330378 A1* | 12/2013 | Parker | A61L 31/16 |
| | | | 435/180 |
| 2016/0115457 A1* | 4/2016 | Kim | A61L 27/3813 |
| | | | 435/373 |
| 2016/0318260 A1* | 11/2016 | Hyde | B33Y 10/00 |

FOREIGN PATENT DOCUMENTS

| WO | WO 2011/028579 A2 | 3/2011 |
|---|---|---|
| WO | WO 2015/069619 A1 | 5/2015 |

OTHER PUBLICATIONS

Hinton, et al., "Three-dimensional printing of complex biological structures by freeform reversible embedding of suspended hydrogels," Sci. Adv. vol. 1(9), 2015, pp. 1-10.
Jang, Jinah, "3D Bioprinting and In Vitro Cardiovascular Tissue Modeling," Bioengineering, vol. 4(71), 2017, pp. 1-20.
Khan, et al., "Evaluation of Changes in Morphology and Function of Human Induced Pluripotent Stem Cell Derived Cardiomyocytes (HiPSC-CMs) Cultured . . . ," PLOS One, 2015,pp. 1-19.
Kolesky, et al., "3D Bioprinting of Vascularized, Heterogenous Cell-Laden Tissue Constructs," Adv. Mater. vol. 26, 2014, pp. 3124-3130.
Ong, et al., "Biomaterial-Free Three-Dimensional Bioprinting of Cardiac Tissue using Human Induced . . . ," Scientific Reports, vol. 7(4), 2017, pp. 1-11.
Wang, et al., "A simple and high-resolution stereolithography-based 3D bioprinting . . . ," Biofabrication, vol. 7, 2015, pp. 1-11.
Ye, et al., "Scalable Unit for Building Cardiac Tissue," Adv. Mater. vol. 26 (42), 2014, pp. 7202-7208.

* cited by examiner

*Primary Examiner* — Micah Paul Young
(74) *Attorney, Agent, or Firm* — Kory D. Christensen

(57) ABSTRACT

A cardiac patch for treatment of a mammalian heart including perfusable vessels embedded integratedly between two layers of anisotropically oriented myocardial fibers. The cardiac patch is made using a dual 3D bioprinting technique using stereolithography to form an anisotropic construct and extrusion printing to form perfusion vessels. A nutrient and oxygen containing media can be provided within the perfusion vessels for growth of cells in the cardiac patch. The technique permits larger patches to be made for the treatment of cardiac damage in both small and large mammalian hearts.

22 Claims, 42 Drawing Sheets

FIG. 13E
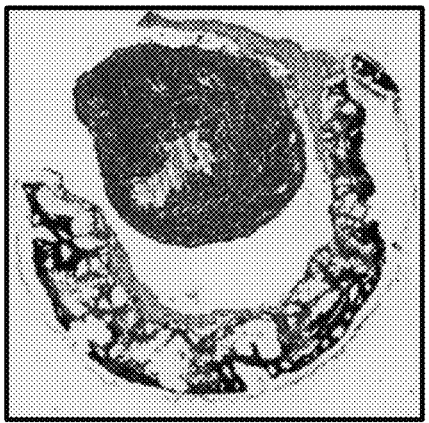
FIG. 13F
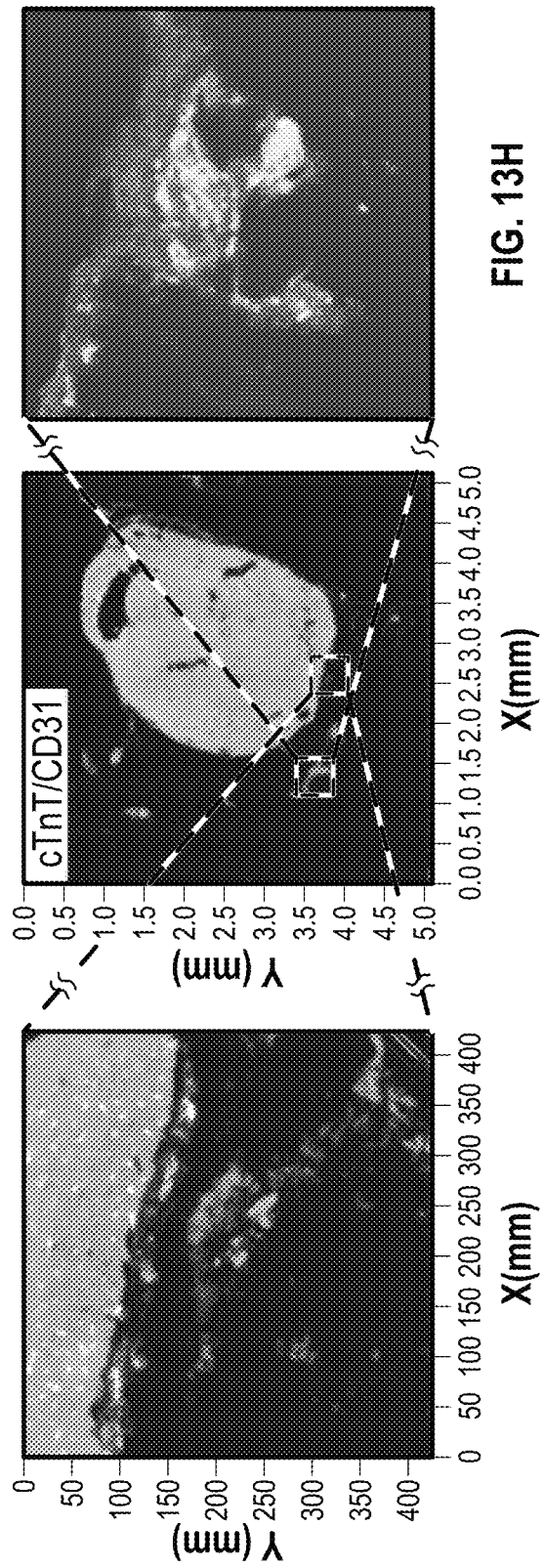
FIG. 13H
FIG. 13G

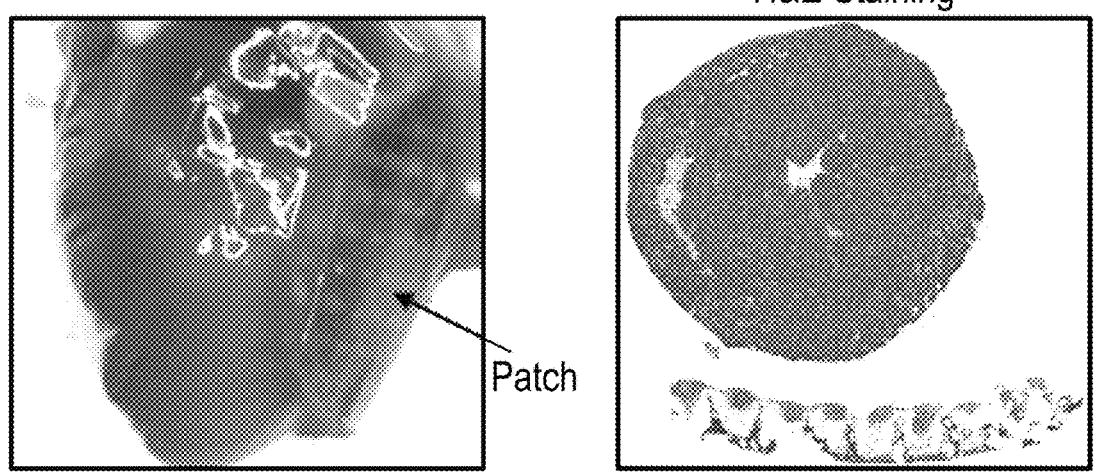
FIG. 14A
FIG. 14B
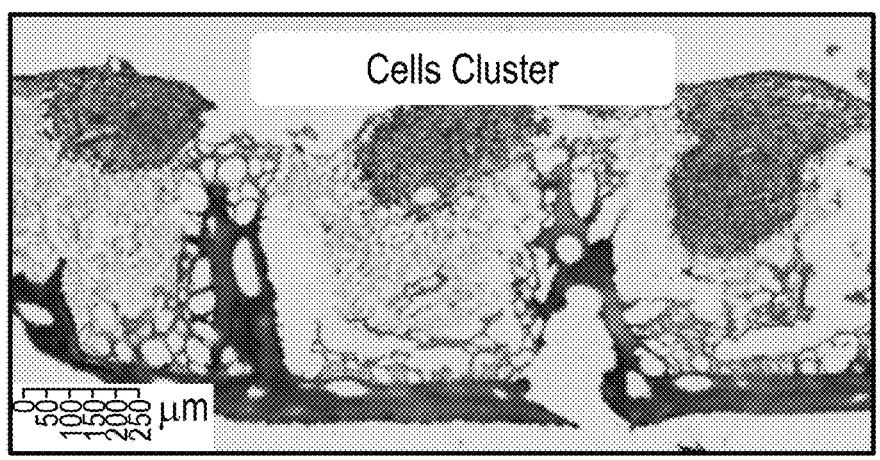
FIG. 14C
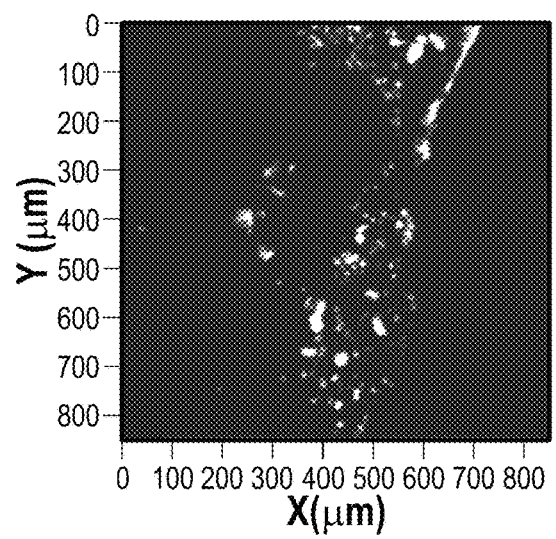
FIG. 14D

MRI Imaging 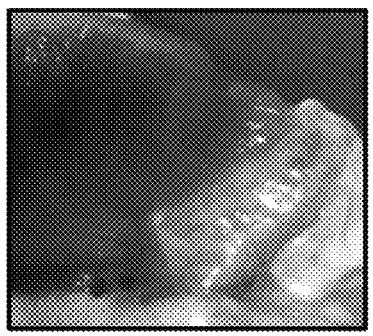 Stereofluorescence
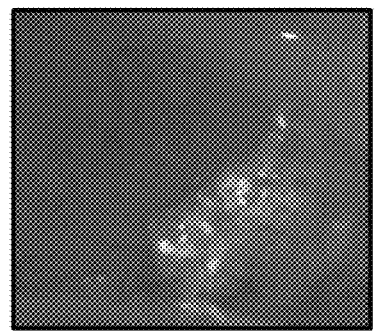
FIG. 15A      FIG. 15B      FIG. 15C
H&E Staining
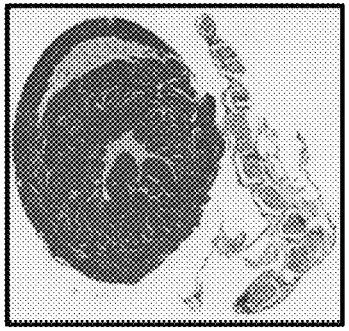
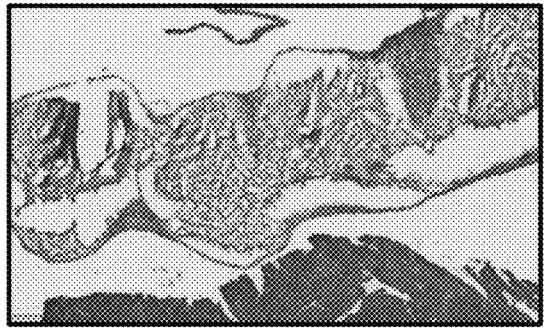
FIG. 15D      FIG. 15E
| Function | LV | RV |
|---|---|---|
| EF % | 65.06 | 53.1 |
| ED vol/ml | 46.18 | 41.22 |
| ES vol/ml | 16.13 | 19.34 |
| ED vol/index | 1.67 | 1.49 |
| ES vol/index | 0.58 | |
| Stroke vol/ml | 30.05 | |
| Stroke vol/index | 1.08 | |
| Output ml/min | 12.53 | |
| ED mass/mg | 78.18 | |
| ES mass/mg | 74.02 | |
FIG. 15F

 
FIG. 18A  FIG. 18B
| Function | LV | RV |
|---|---|---|
| EF % | 62.38 | 58.56 |
| ED vol/ml | 50.84 | 45.45 |
| ES vol/ml | 19.13 | 18.83 |
| ED vol/index | 1.84 | 1.64 |
| ES vol/index | 0.69 | |
| Stroke vol/ml | 31.72 | |
| Stroke vol/index | 1.14 | |
| Output ml/min | 12.69 | |
| ED mass/mg | 77.56 | |
| ES mass/mg | 77.27 | |
FIG. 18C

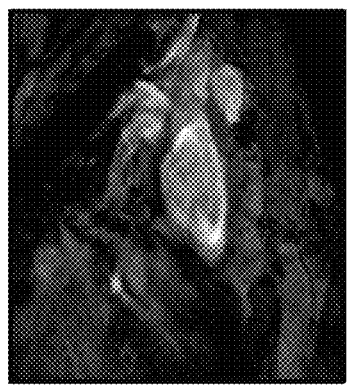 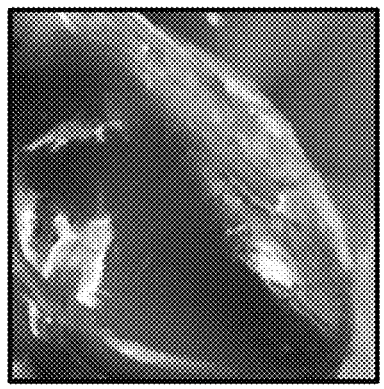 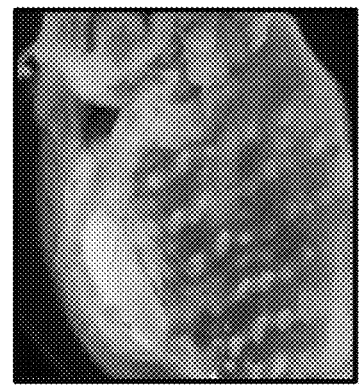
FIG. 19A　　　　　　FIG. 19B　　　　　　FIG. 19C
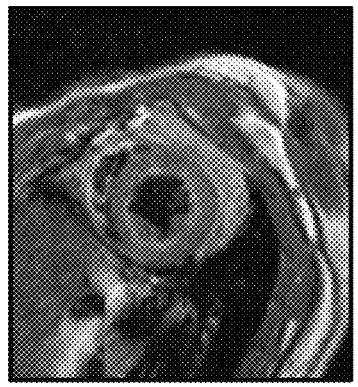 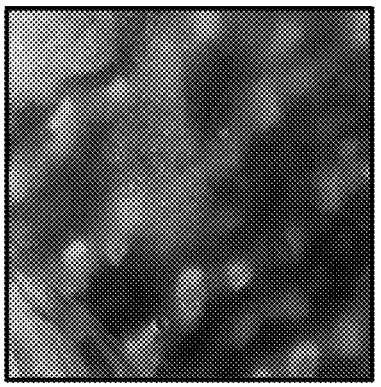 
FIG. 19D　　　　　　FIG. 19E　　　　　　FIG. 19F
| Function | LV | RV |
|---|---|---|
| EF % | 66.28 | 66.88 |
| ED vol/ml | 50.56 | 33.22 |
| ES vol/ml | 17.05 | 11.0 |
| ED vol/index | 2.15 | 1.41 |
| ES vol/index | 0.73 | |
| Stroke vol/ml | 33.51 | |
| Stroke vol/index | 1.43 | |
| Output ml/min | 12.07 | |
| ED mass/mg | 79.47 | |
| ES mass/mg | 78.57 | |
FIG. 19G Angiogenesis in Remodeling Area

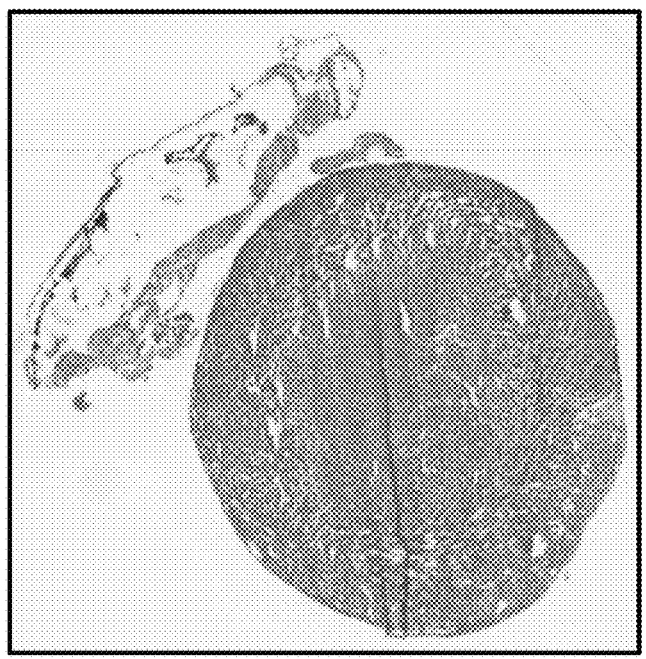
FIG. 22C
FIG. 22B
FIG. 22A

H&E Staining

DAPI Staining
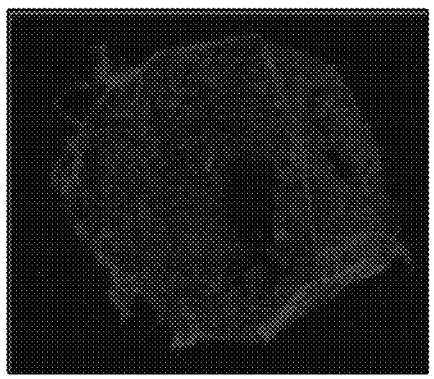
FIG. 26A
GFP Staining
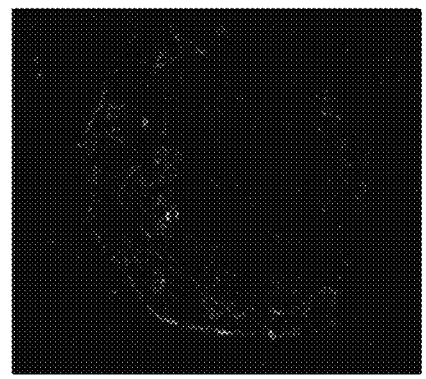
FIG. 26B
cTNT/vWf Staining
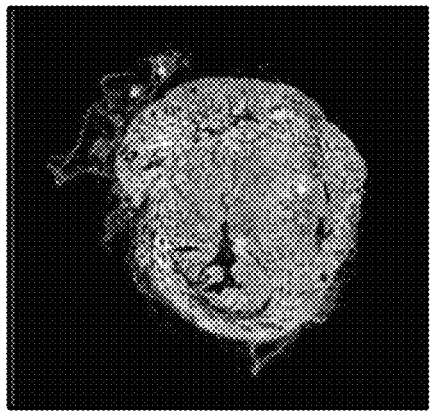
FIG. 26C
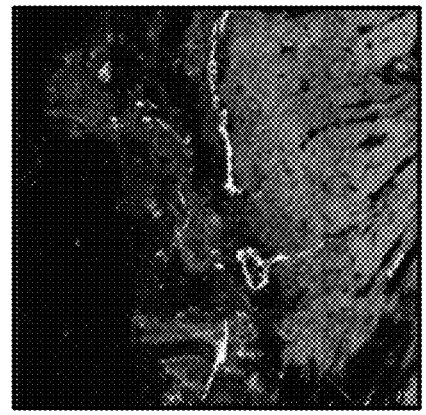
FIG. 26D
| Function | LV | RV |
|---|---|---|
| EF % | 58.13 | 63.37 |
| ED vol/ml | 55.48 | 35.86 |
| ES vol/ml | 23.23 | 13.13 |
| ED vol/index | 2.16 | 1.4 |
| ES vol/index | 0.9 | |
| Stroke vol/ml | 32.25 | |
| Stroke vol/index | 1.25 | |
| Output ml/min | 14.51 | |
| ED mass/mg | 81.84 | |
| ES mass/mg | 92.44 | |
FIG. 26E

HE Staining   MI (Control)

MI (Patch)

MRI Imaging
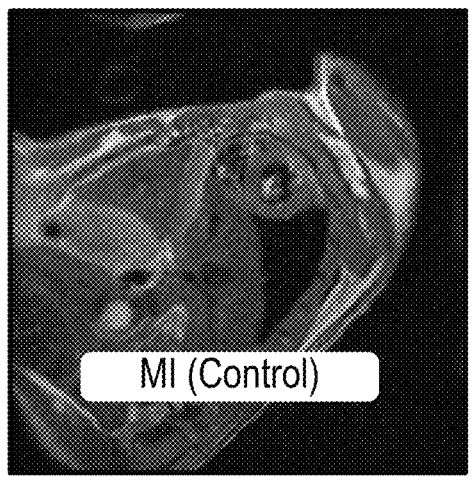
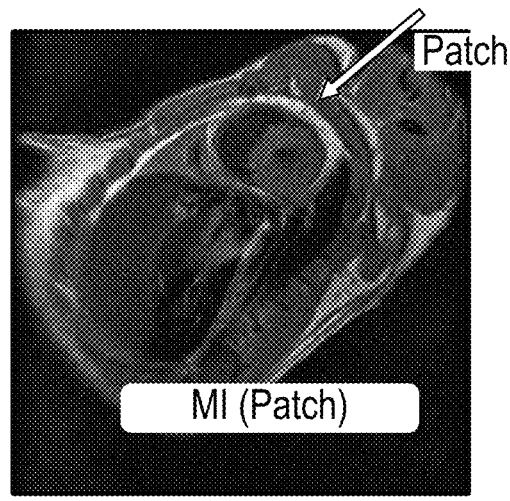
FIG. 27C
FIG. 27D
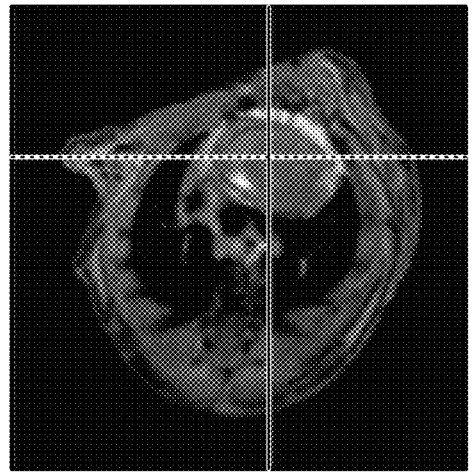
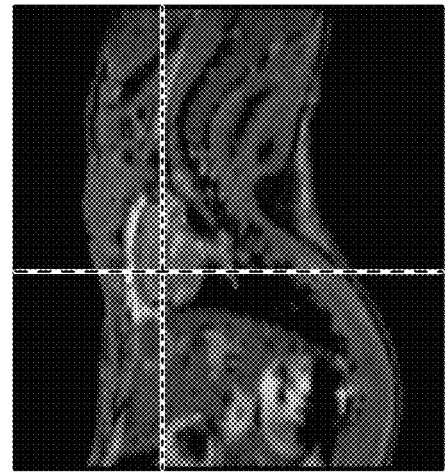
FIG. 27E
FIG. 27F DAPI Staining
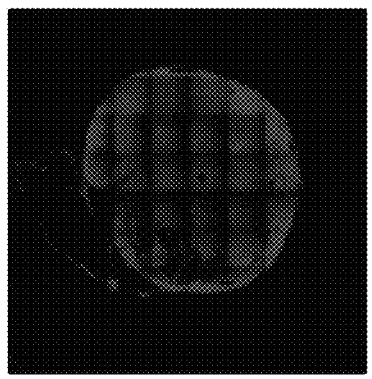
FIG. 28A
GFP Staining
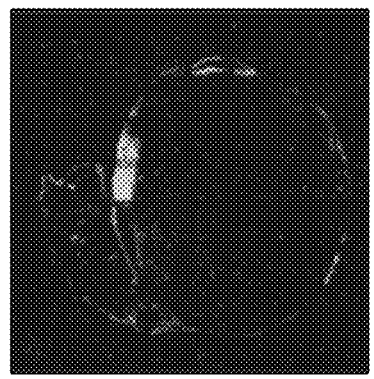
FIG. 28B
cTNT/vWf Staining
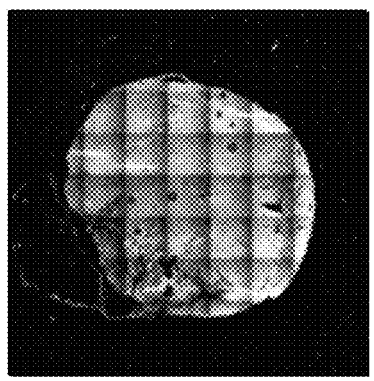
FIG. 28C
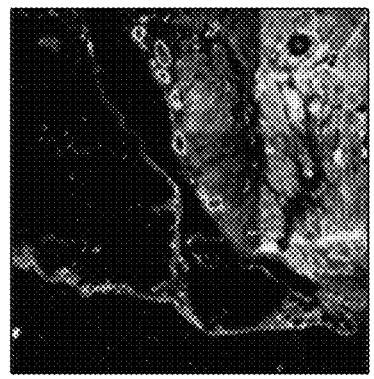
FIG. 28D
| Function | LV | RV |
|---|---|---|
| EF % | 60.85 | 52.61 |
| ED vol/ml | 56.2 | 45.83 |
| ES vol/ml | 22 | 21.72 |
| ED vol/index | 2.04 | 1.74 |
| ES vol/index | 0.8 | |
| Stroke vol/ml | 34.2 | |
| Stroke vol/index | 1.24 | |
| Output ml/min | 16.07 | |
| ED mass/mg | 111.05 | |
| ES mass/mg | 111.54 | |
FIG. 28E HE Staining

FIG. 32C
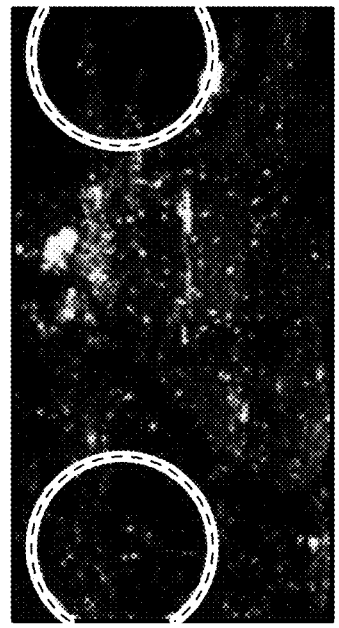
FIG. 32D
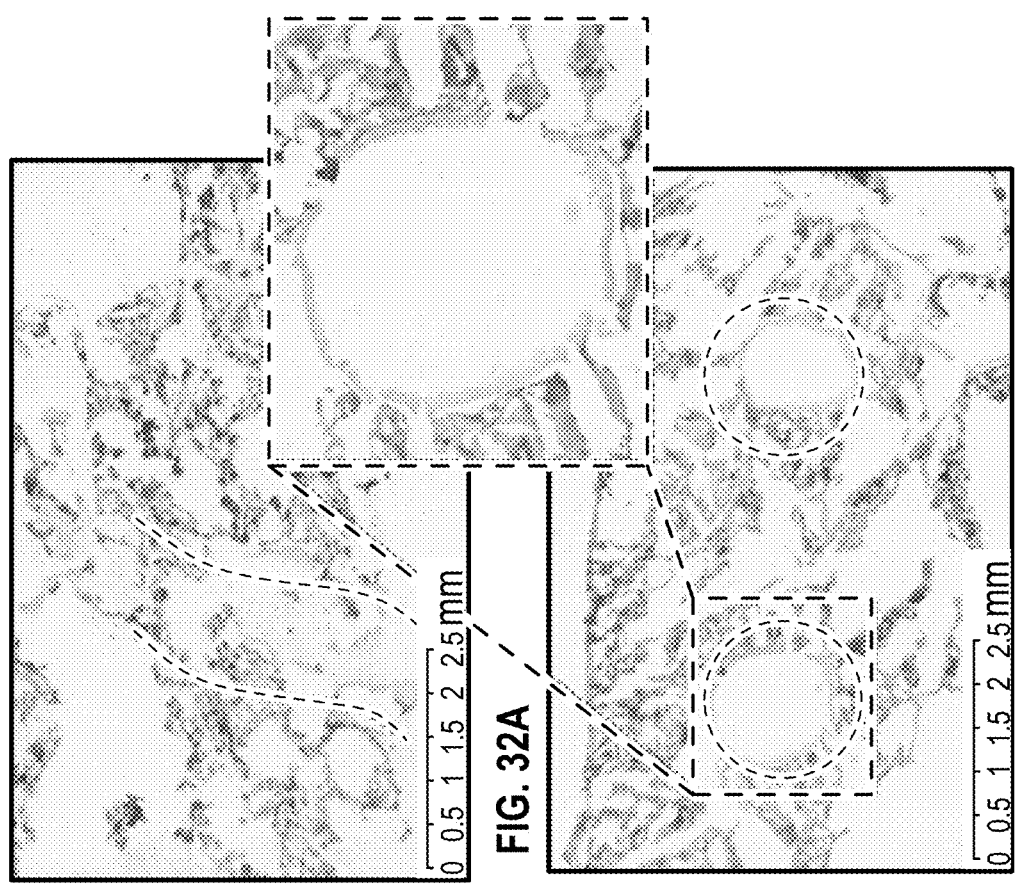
FIG. 32A
FIG. 32B

Anisotropic/Static

Anisotropic/Dynamic/Compression

Isotropic/Static

Isotropic/Dynamic/Compression

Isotropic/Static

Anisotropic/Static

Isotropic/Dynamic/Compression

Anisotropic/Dynamic/Compression

THREE-DIMENSIONAL BIOPRINTING OF CARDIAC PATCH WITH ANISOTROPIC AND PERFUSABLE ARCHITECTURE

CROSS-REFERENCE TO RELATED APPLICATIONS

The present application is a continuation of PCT Application No. PCT/US18/55707, filed Oct. 12, 2018, which claims the benefit of U.S. Provisional Application No. 62/571,684, filed Oct. 12, 2017, each of which is hereby incorporated by reference in its entirety.

STATEMENT OF GOVERNMENT SUPPORT

The present disclosure was made with government support under grant nos. DP2 OD019144-01 awarded by the National Institutes of Health. The government has certain rights in the present disclosure.

BACKGROUND

Cardiovascular disease associated with myocardial infarction (MI) is a major cause of morbidity and mortality worldwide. Adult cardiac muscle is thought to lack the ability to repair and regenerate after MI. Additionally, the death of cardiomyocytes stemming from MI activates an irreversible cascade of events leading to heart failure. Current treatment strategies, such as various drugs and surgical interventions, have their own disadvantages. Current therapeutics, including autografts, allografts, xenografts, and artificial prostheses, have several disadvantages including: donor tissue shortage, immune rejection, anticoagulation therapy, and limited durability. Tissue engineering technique is regarded as an alternative strategy for cardiac repair.

Cardiac patches recently have been developed in some pioneering studies. But current complex or harsh fabrication processes such as the sacrificial template method, high temperature molding, and laser patterned electrospinning, cannot be directly applied to cell-based therapies. Additionally, the heart is a complicated, multicellular tissue with hierarchical, structural and multifunctional characteristics.

Current therapeutics, including autografts, allografts, xenografts, and artificial prostheses, have several disadvantages including: donor tissue shortage, immune rejection, anticoagulation therapy, and limited durability. Tissue engineering techniques are regarded as an alternative strategy for cardiac repair.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which:

FIG. 13E illustrates H&E staining of the cardiac patch for a cardiac patch on a NSG mice (Normal) heart 1 week after implantation;
FIGS. 13F-13H illustrate immunostaining with cTnT/CD31 for a cardiac patch on a NSG mice (Normal) heart 1 week after implantation;
FIG. 14A illustrates an image of a cardiac patch on a NSG mouse (Normal) heart 3 weeks after implantation;
FIGS. 14B and 14C illustrate H&E staining of a cardiac patch on the NSG mouse (Normal) heart 3 weeks after implantation;
FIGS. 14D-14E illustrate GFP staining of a cardiac patch on a NSG mouse (Normal) heart 3 weeks after implantation

FIG. 15A illustrates MRI imaging of a cardiac patch on a NSG mouse (Normal) heart 10 weeks after implantation FIG. 15B illustrates an image of a cardiac patch on a NSG mouse (Normal) heart 10 weeks after implantation FIG. 15C illustrates stereofluorescence of a cardiac patch on a NSG mice (Normal) heart 10 weeks after implantation;

FIGS. 15D-15E illustrate cross-sectional images of a cardiac patch with H&E staining on a NSG mouse (Normal) heart 10 weeks after implantation;

FIG. 15F is a chart containing heart function data of a heart of NSG mice (Normal) heart with an implanted cardiac patch according to the disclosure herein;

FIGS. 18A and 18B show MRI images the NSG mouse heart and cardiac patch;

FIG. 18C is a chart having function data for myocardial remodeling at 6 weeks post implantation for the heart with the electrical burn injury;

FIGS. 19A-19F illustrate images regarding myocardial remodeling at 10 weeks after implantation of a cardiac patch on a NSG mouse heart having post-electrical burning injury;

FIG. 19G is a chart having data for heart function for a NSG mouse heart having post-electrical burning injury remodeling at 10 weeks after implantation of a cardiac patch;

FIG. 22A illustrates H&E staining of the cardiac patch and NSG mouse heart having MI 1 day after implantation;

FIG. 22B illustrates a picture of a heart with a cardiac patch thereon;

FIG. 22C illustrates H&E staining of the cardiac patch on a NSG mouse heart having MI 6 weeks after implantation

FIG. 26A illustrates DAPI staining of a cardiac patch on a NSG mouse heart having MI 10 weeks after implantation;

FIG. 26B illustrates GFP CD31 staining of a cardiac patch on a NSG mouse heart having MI 10 weeks after implantation;

FIGS. 26C-26D illustrate CTnT/vWf staining of a cardiac patch on a NSG mouse heart having MI 10 weeks after implantation;

FIG. 27D is a chart having data of heart function for a NSG mouse heart at 10 weeks after implantation;

FIG. 27C-F illustrate MRI imaging of a NSG mouse heart having MI 4 months after implantation of a cardiac patch;

FIGS. 28A-28D illustrate staining for the cardiac patch at 4 month implantation for a NSG mouse heart having MI;

FIG. 28E is a chart having data of heart function for a NSG mouse heart having MI at 4 months after implantation;

FIGS. 32A and 32B illustrate H&E staining of a thick cardiac anisotropic patch;

FIGS. 32C and 32D illustrate immunostaining of a thick cardiac anisotropic patch;

DETAILED DESCRIPTION

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. It should be understood at the outset that although illustrative implementations of one or more embodiments are illustrated below, the disclosed compositions and methods may be implemented using any number of techniques. The disclosure should in no way be limited to the illustrative implementations, drawings, and techniques illustrated herein, but may be modified within the scope of the appended claims along with their full scope of equivalents.

Figure 1A:
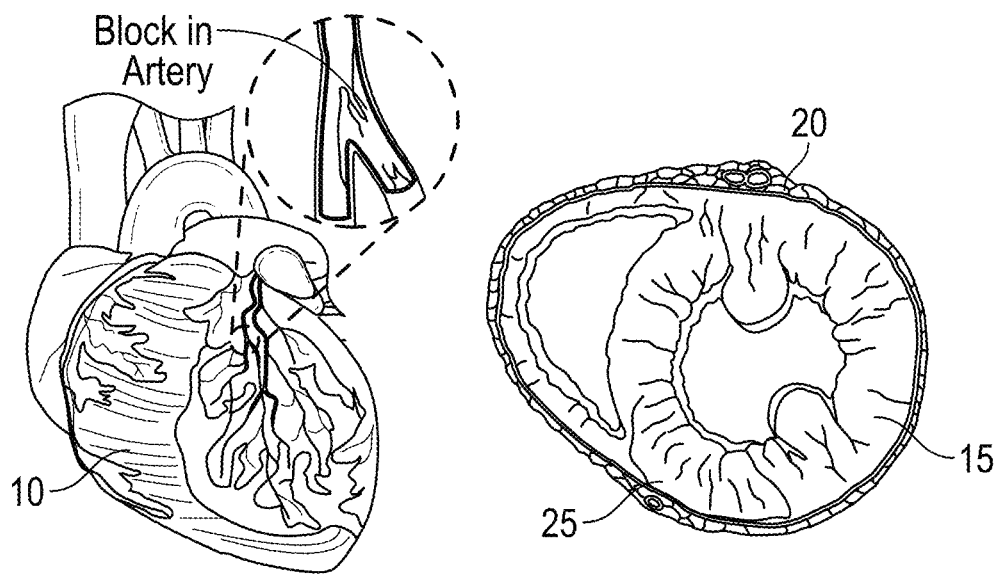
FIG. 1A illustrates a typical mammalian heart.
Figure 1B:
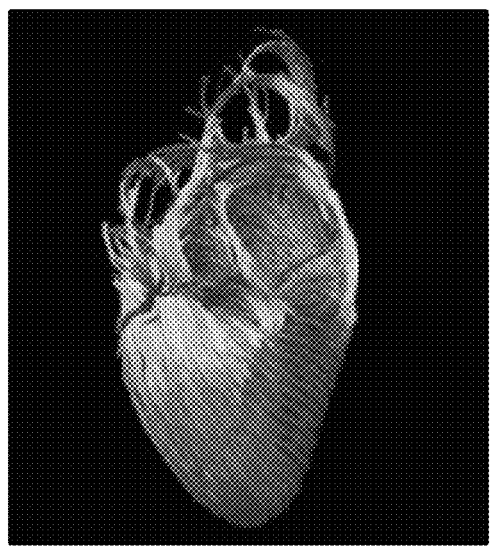
FIG. 1B illustrates the anisotropy of the heart.
Figure 1C:
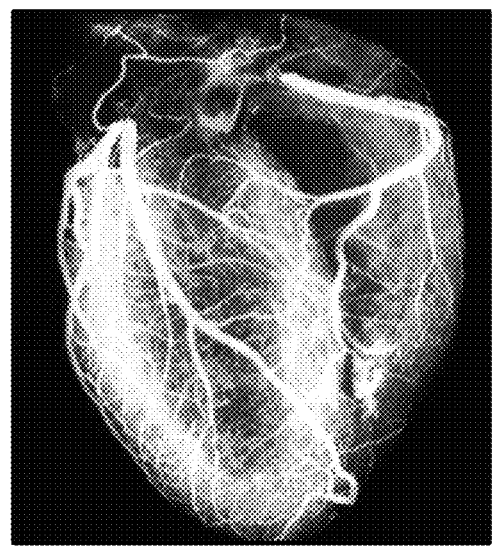
FIG. 1C illustrates the vasculature of the heart.

Within the native heart, cardiac muscle fibers are surrounded by and coupled to endomysial collagen sheaths that are bundled within a honeycomb-like network of undulated perimysial collagen fibers. These features yield directionally dependent electrical and mechanical properties collectively termed cardiac anisotropy. The anisotropic architecture of the heart muscle enables efficient pumping of blood, exemplified by the fiber angle and orientation of cardiomyocytes within the extracellular matrix (ECM), enabling torsional squeezing to maximize ejection fraction. Therefore, the anisotropic structural design is considered herein in the cardiac construct fabrication of the cardiac patch disclosed herein, capable of performing an oriented myocardial fiber distribution. As illustrated in FIG. 1B, the heart has anistropic myoardial fibers for oriented contraction. Moreover, as shown in FIG. 1C the heart has perfusable (blood) vessels to maintain metabolism.

The heart may become damaged during certain cardiac events such as MI, leading to damaged cardiac muscle tissue. For instance, as shown in FIG. 1A, a heart 10 has cardiac muscle fibers 15 surrounded by collagen sheath 20. As a result of MI or other cardiac event, muscle damage 25 to the muscle fibers 15 as well as an artery block can arise.

Based on biological and anatomical understanding of myocardial tissue, developed herein is a functional cardiac tissue with anisotropic myocardial fibers and perfusable vasculature for cardiac tissue regeneration which may be made in a thick patch construct. This provides a strategy for obtaining a multi-cellularized cardiac patch with biomimetic characteristics that is suitable for cardiovascular disease treatment.

In particular, disclosed herein is a three-dimensional (3D) bioprinting technique to directly fabricate a vascularized cardiac patch with both anisotropic fiber and perfusable vessel architecture. The design integrates biomimetic aligned myocardial fibers and perfusable blood vessels to create a thick, functional cardiac patch, suitable for human heart implantation. Due to the anisotropic contraction properties, the patch not only provides a physical support to prevent dilation of the heart wall, but also improve cardiac tissue regeneration. 3D bioprinting not only can accomplish this anisotropy through computer aided design (CAD), but also, cells can be directly encapsulated into the constructs to form cellularized tissue. Moreover, 3D bioprinting enables a thick patch fabrication suitable to implant into human body.

Currently, most studies on pre-vascularization focus on simple patterns, or capillaries in the thin cardiac patches. Perfusable vasculature with complex hemodynamic capacity has yet to be developed within cardiac patches. 3D bioprinting as disclosed herein is able to fabricate perfusable vessels with any geometrical pattern. The cardiac patch disclosed herein combines multiple features including, large thickness of the patch suitable for humans, anisotropic myofibers, perfusable vessels, and dual bioprinting fabrication method.

Specifically, disclosed herein is an integrated manufacturing technique that combines stereolithographic 3D printing and extrusion 3D printing to directly fabricate a biomimetic cardiac patch which has greater thickness than conventional patches. In order to mimic the native myocardial configuration, a "sandwich" cardiac patch was developed, where layers of perfusable vessels are embedded between layers of anisotropic fibers. This construct is formed using dual bioprinting, where the anisotropic myofibers are printed by stereolithography (SLA), and the vessels are printed by extrusion printing.

The anisotropic fibrous layer structure formed using SLA may employ a mixed bioink of gelatin methacrylate (GelMA) and polyethylene glycol diacrylate (PEGDA) to print the fiber layers. The bioink further includes pluripotent stem-cell cardiomyocyte (iPS-CMs), which are capable of differentiating into and forming the cardiac muscle of the cardiac patch. Accordingly, with this method, iPS-cardiomyocytes laden anisotropic honeycomb fibers are printed using SLA with the mixed bioink.

In between layers of anisotropically oriented myocardial fibers, the perfusable vessels are formed using extrusion printing with a fugitive bioink, such as Pluroic F127. Human umbilical vein endothelial cells (HUVECs) are included in the fugitive bioink, which may form the walls of the vessels. The vessels have a geometric design, such as straight, furcate, branched and/or tree. Accordingly, extrusion printing is used to form (HUVECs) laden perfusable vessels with geometric design.

In the resultant patches, the perfusable vessels embedded in the anisotropic fibers transfer nutrients and oxygen for cell viability and development. This perfusion and delivery of needed components permits greater success of the patch and furthermore, the development and use of thicker patches. The heart is among those organs with the highest ratio of vessels to cardiomyocytes, where capillaries sprouting from large vessels are adjacent to every cardiomyocyte constantly providing oxygen and nutrients to the tissue. Thus, for successful cardiomyocyte transplantation, vasculature provides for the survival and function of larger scale, thick engineered cardiac tissues after implantation.

Figure 2A:
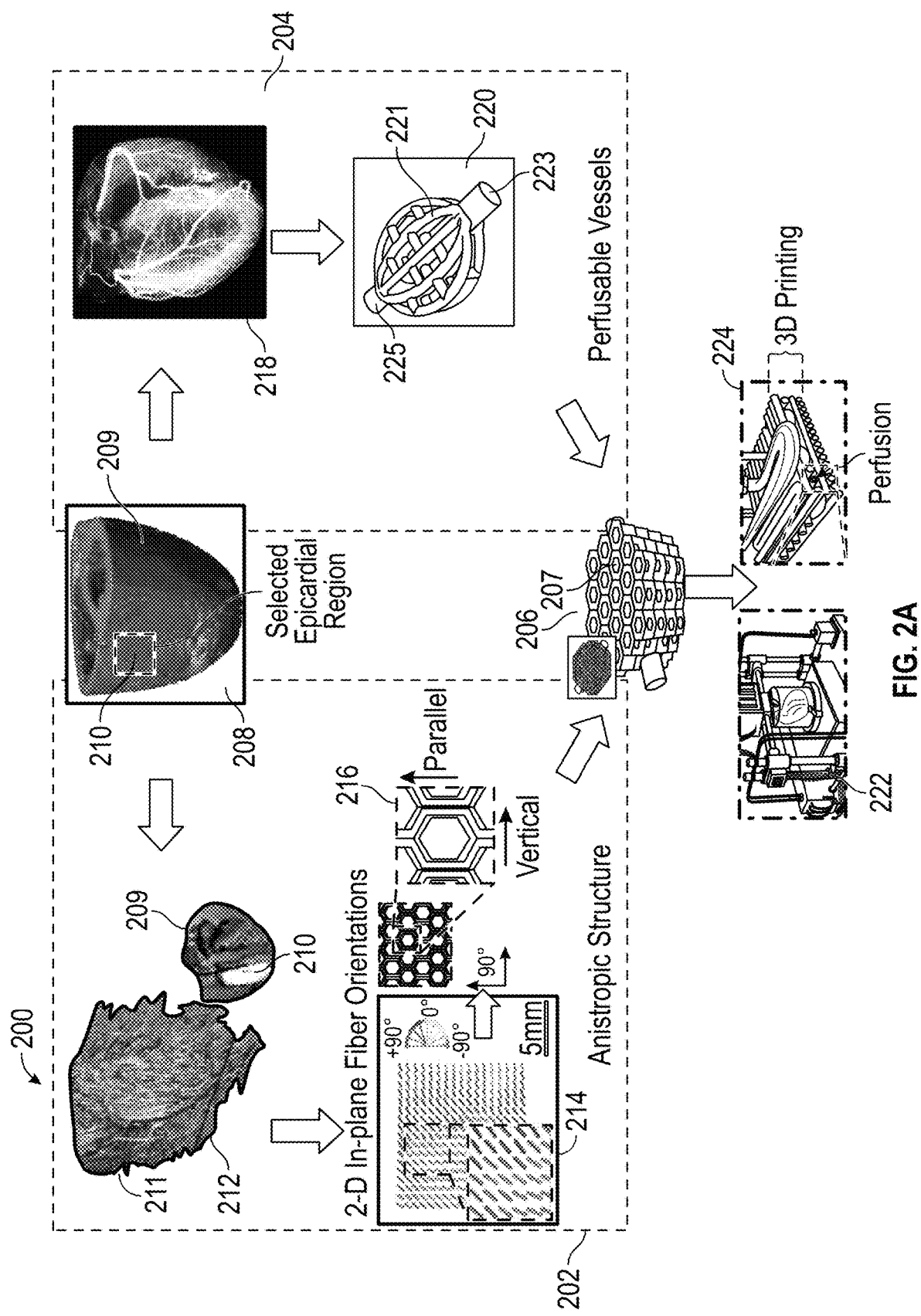
FIG. 2A illustrates an embodiment of a dual bioprinting scheme of an anisotropic cardiac patch with perfusion vessels according to the disclosure herein.

FIG. 2A illustrates a flow diagram 200 for formation of the 3D printed cardiac patch disclosed herein. The flow diagram 200 illustrates a dual bioprinting flow having a scheme 202 for formation of an anisotropic structure, and scheme 204 for formation of perfusable vessels, which result in the formation of a cardiac patch at step 206. Flow diagram 200 includes arrows which show the direction in steps of the flow. Illustrated in step 208 is a heart 209 having a selected epicardial region 210 for repair. The epicardial region 210 may have damage from coronary heart disease, MI, or other cardiac event.

As shown in step 212, the selected epicardial region 210 has an anisotropic fiber orientation 211. As illustrated in step 214, a two dimensional (2D) in plan fiber orientation is provided to mimic the anistropic fiber orientation 211. In step 216, there is shown the hexagonal structure in which the anistropic structure will be printed, resulting in a honeycomb like structure. Although a hexagonal example is shown, any polygonal structure or geometric pattern may be used which can be printed anistropically.

Turning now to scheme 204 for formation of perfusable vessels, step 218 illustrates the vascular imaging of heart 209. Step 220 illustrates a perfusable vessel structure 221 which may be printed via extrusion printing. The perfusable vessel structure 221 has an inlet 223 for nutrient and oxygen containing media and an outlet 225. Although perfusable vessel structure 221 is shown as a distinct structure in step 220, in practice it will be printed integratedly between layers of the anistropic structure. Step 206 illustrates a resulting cardiac patch 207 having the perfusable vessels embedded of scheme 204 between layers of the anistropic structure of scheme 202.

Figure 2B:
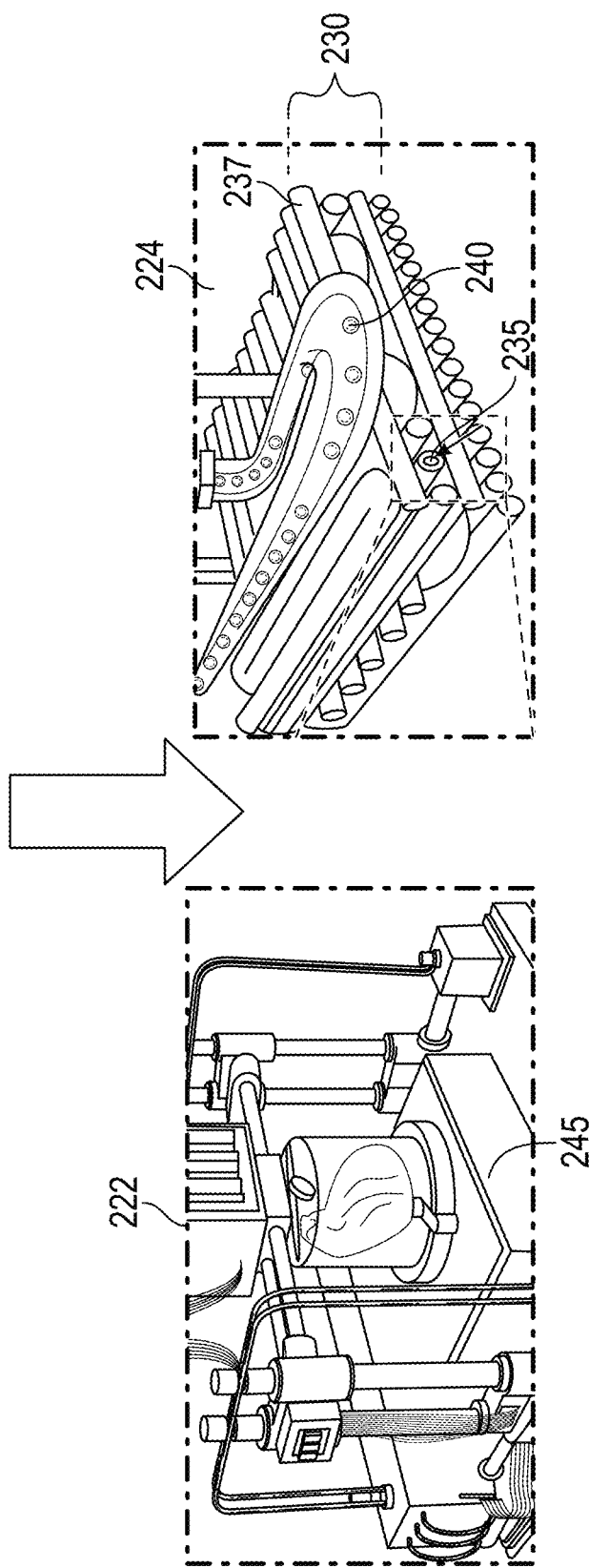
FIG. 2B illustrates an expanded view of an embodiment of a dual bioprinting scheme of an anisotropic cardiac patch with perfusion vessels according to the disclosure herein.

Step 224 of FIG. 2A illustrates how the bioprinting of both the anistropic structure and the perfusable vessel structure is printed together. FIG. 2B shows steps 222 and 224 of FIG. 2A expanded. As illustrated in step 224 of FIG. 2B, a fugitive bioink 240 is being printed on top of and between layers of the anisotropic structure 237. The perfusable vessel 235 is shown embedded within the structure. Again, step 222 of FIG. 2B shows a bioprinter 245 for forming a heart or cardiac patch.

Figure 3:
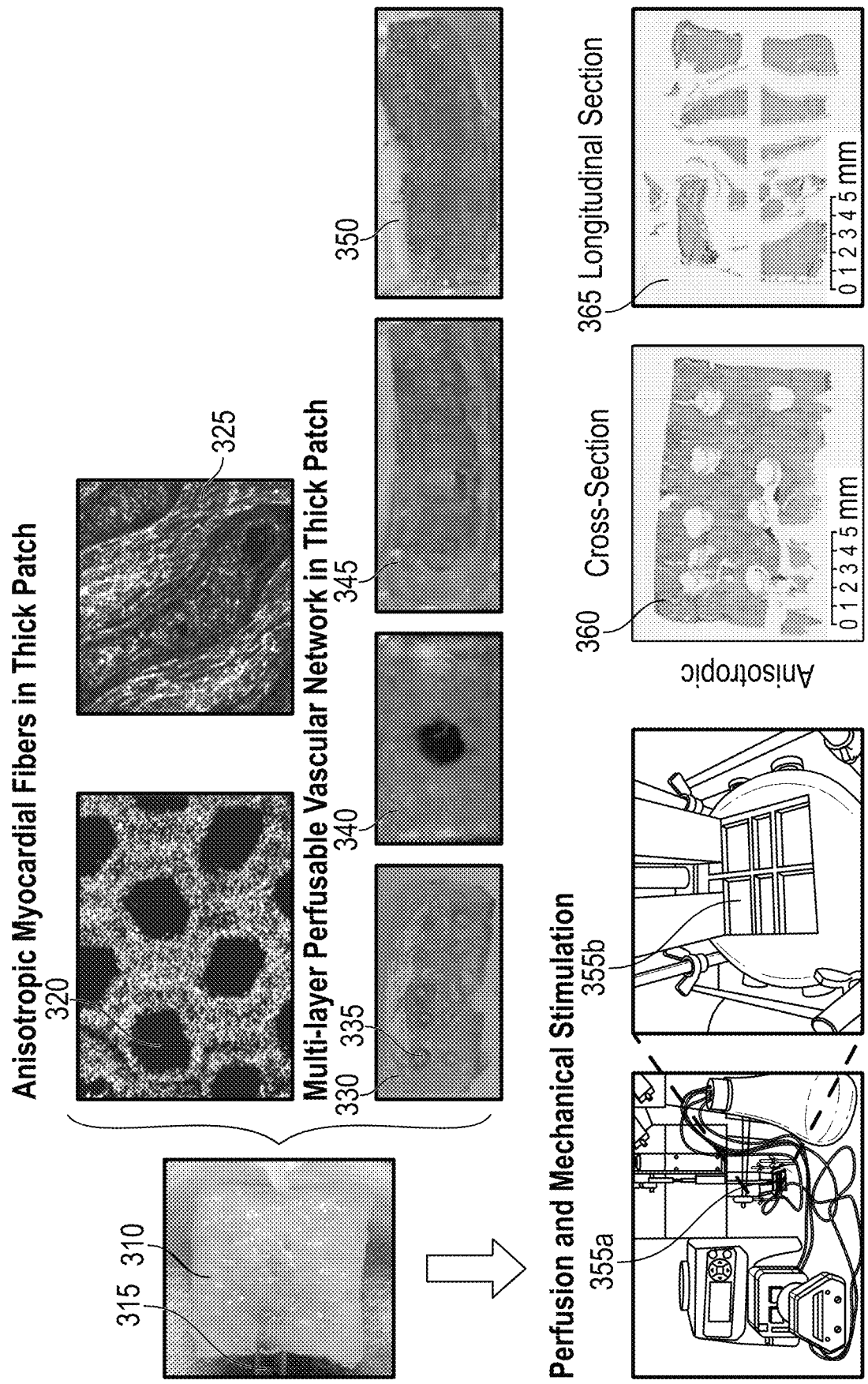
FIG. 3 illustrates an embodiment of a cardiac patch and its formation according to the disclosure herein.

FIG. 3 provides an image of a cardiac patch 310 having an inlet 315. The hexagonal structure is shown in the staining image 320 along with its anisotropic character in image 325. An image of the cardiac patch 330 is shown with open perfusion vessels 335 having provided with staining thereby illustrating each having an internal hollow throughbore for perfusion of a medium. Further images 340, 345, and 350 illustrate perfusion in the cardiac patch 330 with medium as a result of the multi-layer vascular network in the cardiac patch created by the perfusion vessels. The cardiac patch 330 may be two layers with large vessels of 5 mm or small vessels of 2 mm, which can be adjusted depending on the size of the organ, heart or mammal/animal. A red dye may also be used to illustrate perfusion through the cardiac patch 330 in images 340, 345, and 350. The anisotropy of the cardiac patch is further illustrated in cross-section image 360 of a cardiac patch and further in longitudinal section image 365.

For the structure of the cardiac patch, the outer layers may include hydrogel with anisotropic myocardial fibers. The hydrogel may mimic natural tissue and be biocompatible. In particular, the hydrogel may be GelMA and PEGDA, but may be any suitable natural or synthetic biocompatible hydrogel, such as those derived from collagen, matrigel, hyaluronic acid, chitosan, dextran and alginate acid, among others. The hydrogel may include polymers and copolymers of acrylic acid, polyethylene oxide, acrylamide, lactic acid and derivatives and combinations thereof. The outer layers and hydrogel may be laden with cells of a predetermined type depending on the desired tissue construct. For instance, for use with a heart, cardiac muscle cells and/or cardiomyocytes, and iPS-CMs may be employed. Any other mammalian cells may be employed including stem cells, as well as types which make up or form organs, bones, skin, blood or other connective tissue, including mesenchymal stem cells (MSCs), embryonic stem cells (ESCs), cardiac fibroblasts, and endothelial cells, and mixtures thereof. The aforementioned cells may be cocultured together, for instance, a coculture of endothelial cells and cardiomyocytes may be made to capillaries in the fibers of the construct.

During the fiber fabrication via stereolithography, the perfusion vessels may be extruded on the anisotropic fibers. The perfusion vessels may be formed with a fugitive ink. The fugitive ink may be a thermosensitive hydrogel which may serve as structural support for forming the tubular blood vessel during synthesis. Exemplary fugitive inks may include a copolymer of hydrophobic polypropylene oxide (PPO) and hydrophilic polyetheylene oxide (PEO), and may be a PEO-PPO-PEO triblock copolymer. An exemplary commercially available fugitive ink includes Pluronic® F127 bioreagent. The fugitive ink is a gel at room temperatures but may transform to a solution at low temperature or be dissolved in water for removal. In this way, the fugitive ink can be laid as a gel between the anisotropic fibers, and then removed via dissolution and/or temperature and washed away, thereby leaving a hollow vessel for perfusion. The fugitive ink may be laden with any type of cell which assists in forming the walls of the perfusion vessel. The fugitive ink may be laden with HUVECs or other cells which may form a strong wall for the perfusion vessels, such as human or mammalian cells, and may include endothelial cells, vascular endothelial cells, human aortic endothelial cells (HAECs), as well as other suitable cells.

The cardiac patch disclosed herein may be formed in layers, printing the perfusion vessel layers integratedly between layers of the anisotropic fibers, which may be myocardial fibers. For example, myocardial fibers may be printed (in hexagon pattern for example) for 5 layers using stereolithgraphy. Then perfusion vessels may be printed thereon for 1 layer using extrusion printer. After that, printing may be continued with the myocardial fibers for 5 more layers, followed by 1 layer of perfusion vessels, which may be continued until the desired patch size is obtained. Any plurality of layers may be used from 2 to 5, or from 2 to 50. In this way the perfusion vessels can be embedded integratedly in the middle of patch. In other embodiments, the myocardial fibers layers and perfusion vessel layers can alternate. In other embodiments, there can be 2, 3, 4, 5, 6, 7, or 8 layers of myocardial fibers followed by 1, 2, or 3 layers of perfusion vessels. In other embodiments, there may be from 1 to 10 layers of mycordial fibers, followed by 1-5 layers of perfusion vessels. In this way the vasculature can be provided throughout the resulting anistropic structure permitting broad perfusion and support of nutrient and oxygen media.

As illustrated herein, 3D bioprinting is one of the most feasible techniques for creating complicated implants with macro/micro features. The 3D bioprinting of the construts may be accomplished through computer aided design (CAD), and also cells can be directly encapsulated into the constructs to form cellularized tissue.

While 3D printed patches have been formerly developed, such studies have focused on the fabrication of very thin patches. Thin patches are not suitable for the human heart, especially for thick cardiac tissue regeneration. Accordingly, disclosed herein is a perfusable, geometric vasculature with complex hemodynamic capacity provided within the thick cardiac constructs. This geometric vasculature with complex hemodynamic permits thicker and larger cardiac patches than has been conventionally allowed.

The cardiac patch disclosed herein may be made as a thin patch, or as a thick patch. Thickness (also referred to as thinness or height) may in this case be considered the dimension normal to the surface on which it is implanted, such as a heart of a mammal. A thin patch may range from about 200 μm to less than 1 mm in at least one dimension (such as thickness), about 200 μm to about 0.8 mm in at least one dimension (such as thickness), to about 0.25 mm to about 0.5 mm in at least one dimension (such as thickness), and combinations of the aforementioned. The thick patch may include a range of at least 1 mm to 1 cm in at least on dimension (such as thickness), alternatively at least about 1 mm in at least on dimension (such as thickness), alternatively at least about 0.50 cm in at least on dimension (such as thickness), alternatively at least about 0.8 cm in at least on dimension (such as thickness), alternatively at least about 1.5 cm in at least on dimension (such as thickness), alternatively at least about 2.0 cm in at least on dimension (such as thickness), alternatively at least about 2.5 cm in at least on dimension (such as thickness). The thickness of the thick patch may range 1 mm to 1 cm in thickness. For instance, the thickness of a thick cardiac patch may be any of the aforementioned thicknesses, while its length and width may be at least about 1 cm, or alternatively at least about 2 cm, or alternatively range from about 2 cm to about 5 cm. For the thin patch, its thickness may range from 200 μm to less than 1 mm, while its length and width may be at least about 2 mm, or alternatively range from 2 mm to 8 mm. The thin patch may be sized for a mouse heart, whereas the thick patch sized for a larger mamal heart such as a human. For both thick and thin patches, the thickness should be less than each of the length and width.

The patch may take any shape such as spherical or hexahedron, cubic, rectangular cuboid, or other. The dimensions may include for instance, independently of one another, about 200 µm to about 5 cm, alternatively 1 mm to about 3 cm alternatively from 0.8 cm to about 1 cm, in length, width, and/or height (wherein height is thickness). For instance, for a thick patch, the dimensions may include (length×width×height in cm (hereinafter L×W×H)) 1×1×1, 1×2×1, 1×1×2, 2×2×1, 2×1×2, 1×2×2, or other dimensional sizes. The H may range from 1 mm to 1 cm, or alternatively from 0.5 cm to 1 cm, while L and W may range from at least about 1 cm, or alternatively, range from about 1 cm to about 5 cm, or range from 2 cm to 5 cm. Combinations of each of the aforementioned thicknesses (heights), L and W may be employed.

In the myocardial infarction area, the lost cardiomyocytes are normally replaced by fibroblasts and myofibroblasts which form scar tissue. The formation of this non-contracting fibrous scar alters the workload of the remaining myocardium resulting in remodeling of the heart, leading ultimately to congestive heart failure. The cardiac patch disclosed herein may be placed aside of myocardial infarction area. It provides mechanical support to infarcted myocardium to prevent isochemical pathological cascade. Given that adult cardiomyocytes have a limited capacity for proliferation and regeneration, implanted cardiomyocytes may be provided as disclosed herein to help cardiac repair. The celluarized cardiac patch can also deliver the cells into the infarcted area for cardiac regeneration. Therefore the cardiac patch disclosed herein differs from native cardiac tissue, but has some additional advantages, such as directing cell oriented growth of native cardiac myofibers, transferring mechanical loading with heart beating, as well as maintaining cell viability in the thick patch via perfusable vessels.

The universal design of thick, vascularized cardiac patches is not limited to current printing models, bioinks or cell sources. Based on a patient-specific requirement, further changes to parameters may be made, including printing, bioink, and structural design. While the heart is discussed in the present application, the patch described herein can be used for any organ where an anisotropic perfusable structure is desirable.

EXAMPLES

Thick cardiac patches (1 cm or larger) have been successfully printed. To verify the availability in a biomedical application, the thin patches were firstly tested without perfusable vessels through in vitro and in vivo mice studies. This track was taken because the thin patch is suitable to be implanted into a small animal model. The in vitro study proved that 3D bioprinted patches possessed excellent cardiomyogenesis and angiogenesis. The in vivo evaluation showed implanted cells had high viability and proliferation ability in the cardiac patches disclosed herein. Tissue integration, vessel formation and anastomose after 10 weeks implantation was observed.

The cardiac patches used for the in vitro studies and in vivo with mice are 500 µm in thickness, and 5 mm in length and width, because the mice heart is too small and has no space for implanting thicker patches. The examples involving the thick patch, the thick patch was sized to be 8 mm thick and 2 cm in length and width.

For the present examples, an extrusion printer was used to print geometrical vessels during the patch fabrication, where the temporary, sacrificed material was removed by water or medium to obtain a perfusable, hollow vessel channel. The perfusable vessels were embedded in the anisotropic patch, which is shaped like a sandwich. In our fourth slide, we can see the images of hollow vessels and red dye perfusion. The cardiac patch can be used for cardiovascular disease (CAD) treatment.

In Vitro Studies

Figure 4:
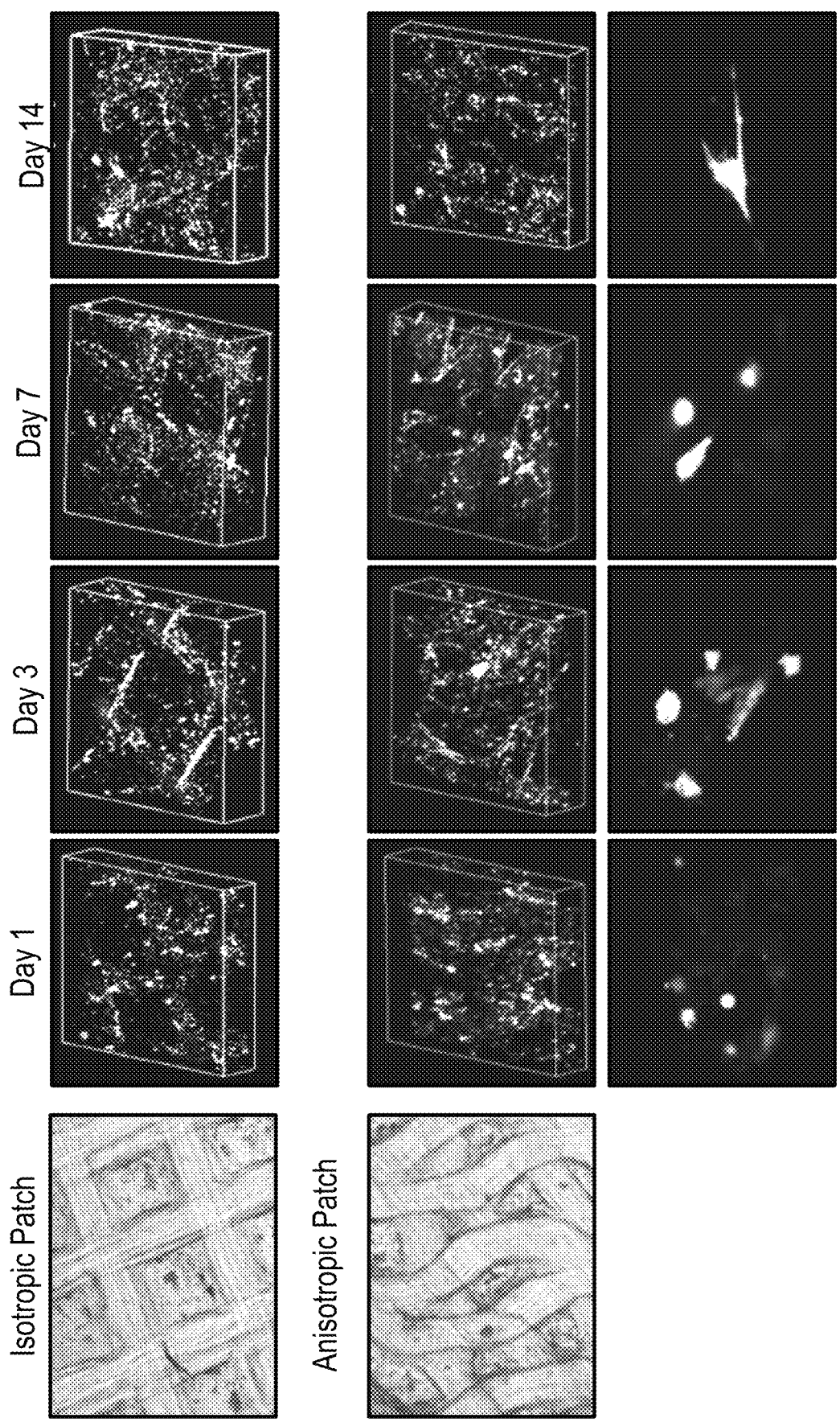
FIG. 4 illustrates the results of an in vitro study to observe the viability of iPS-cardiomyocytes for 14 days.

FIG. 4 illustrates a co-culture of MSC's, HUVECs, and iPS-CMs, with printed anisotropic cardiac patches to observe the viability and beating of iPS-cardiomyocytes for 14 days (days 1, 3, 7 and 14 are shown in vertical columns of FIG. 4 with the respective stained images of the patches for each of isotropic and anisotropic patches) of culture, and isotropic ones to serve as control (comparative). The cells grew well in both the anisotropic and the isotropic patch as illustrated by the staining images within column days 1, 3, 7 and 14.

Figure 5:
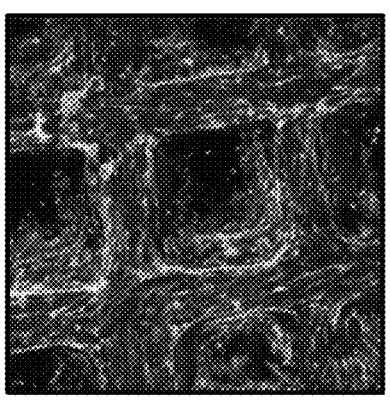
FIG. 5 illustrates anisotropic and isotropic cardiac patches according to the disclosure herein at different cell ratios.
Figure 5:
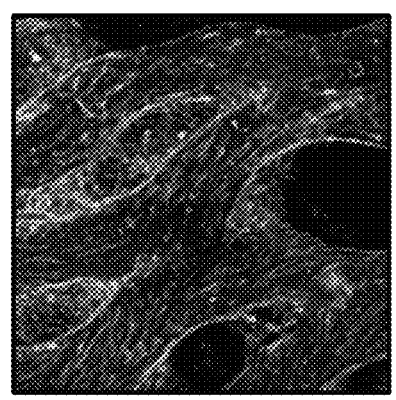
Figure 5:
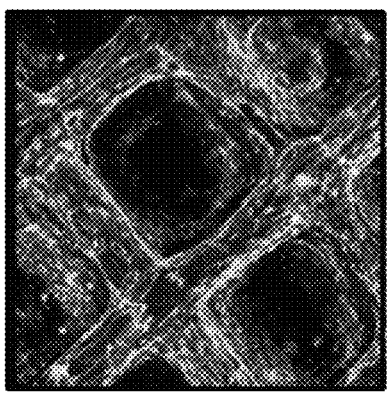
Figure 5:
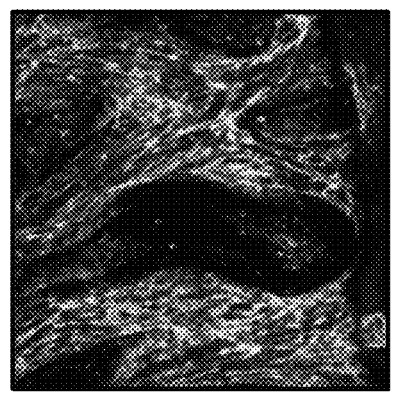
Figure 5:
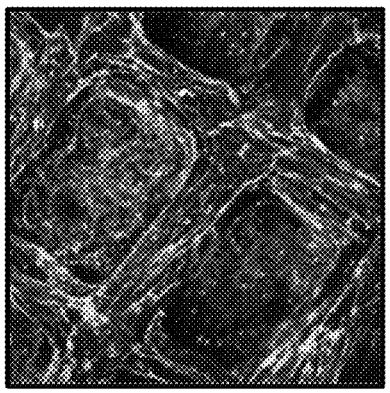
Figure 5:
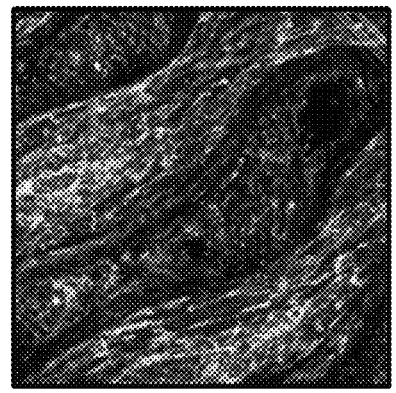

Illustrated in FIG. 5 are anisotropic and isotropic cardiac patches at different cell ratios to optimize co-cultured cell populations including ratios of MSCs/HUVECs/iPS-CM for seven days. As shown by the three columns left to right, the ratios (MSCs/HUVECs/iPS-CM) include 1:2:2, 1:2:3, and 1:2:4, with 1:2:4 being the best one for optimal relative growth of the cardiac tissue and vasculature. Accordingly, the ratio 1:2:4 was employed for further studies.

Figure 6A:
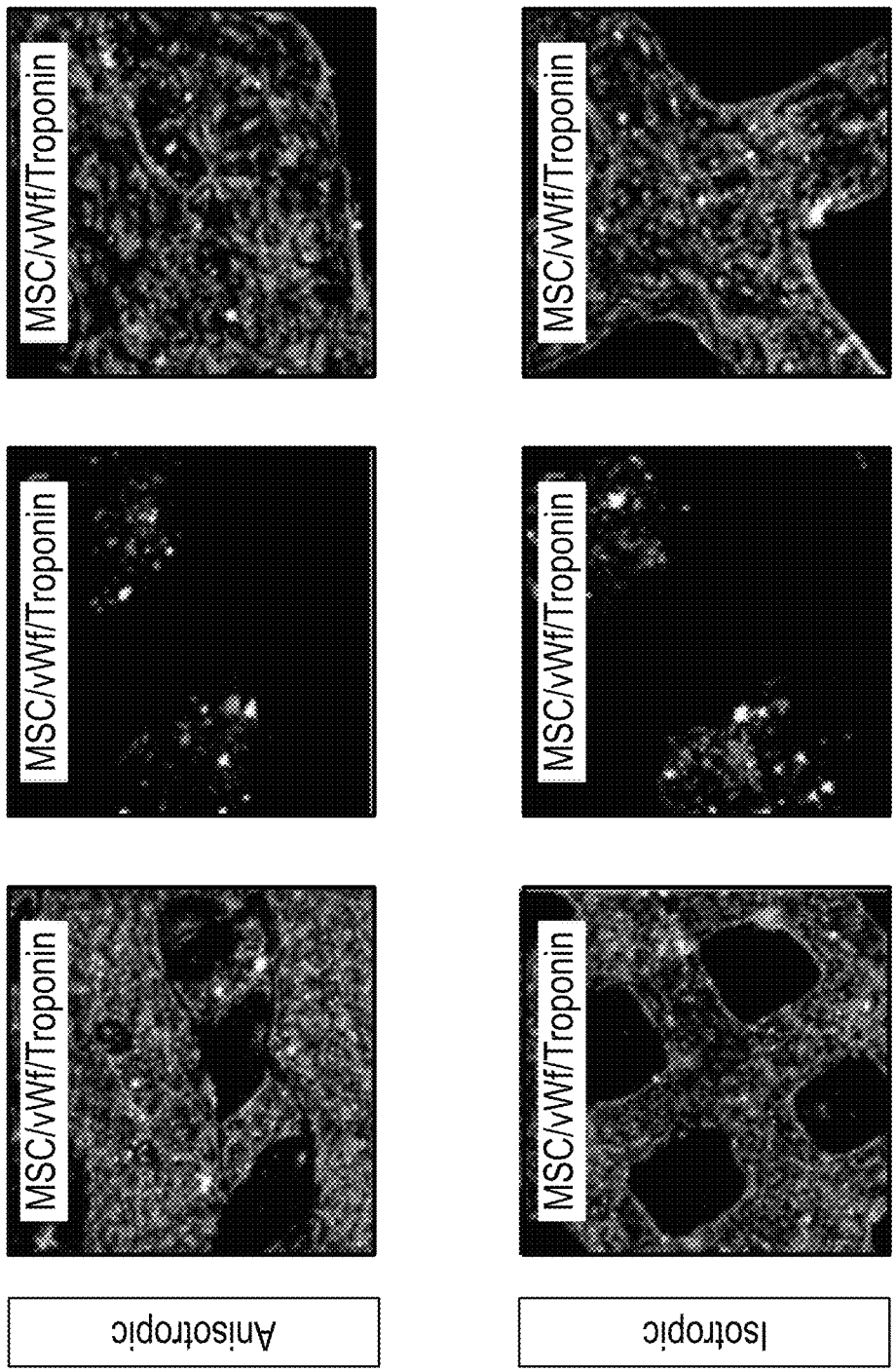
FIG. 6A illustrates cell immunostaining for mesenchymal stem cells (MSC), Von Willebrand factor (vWf), and Troponin for first day post-cells seeding before perfusion culture.
Figure 6B:
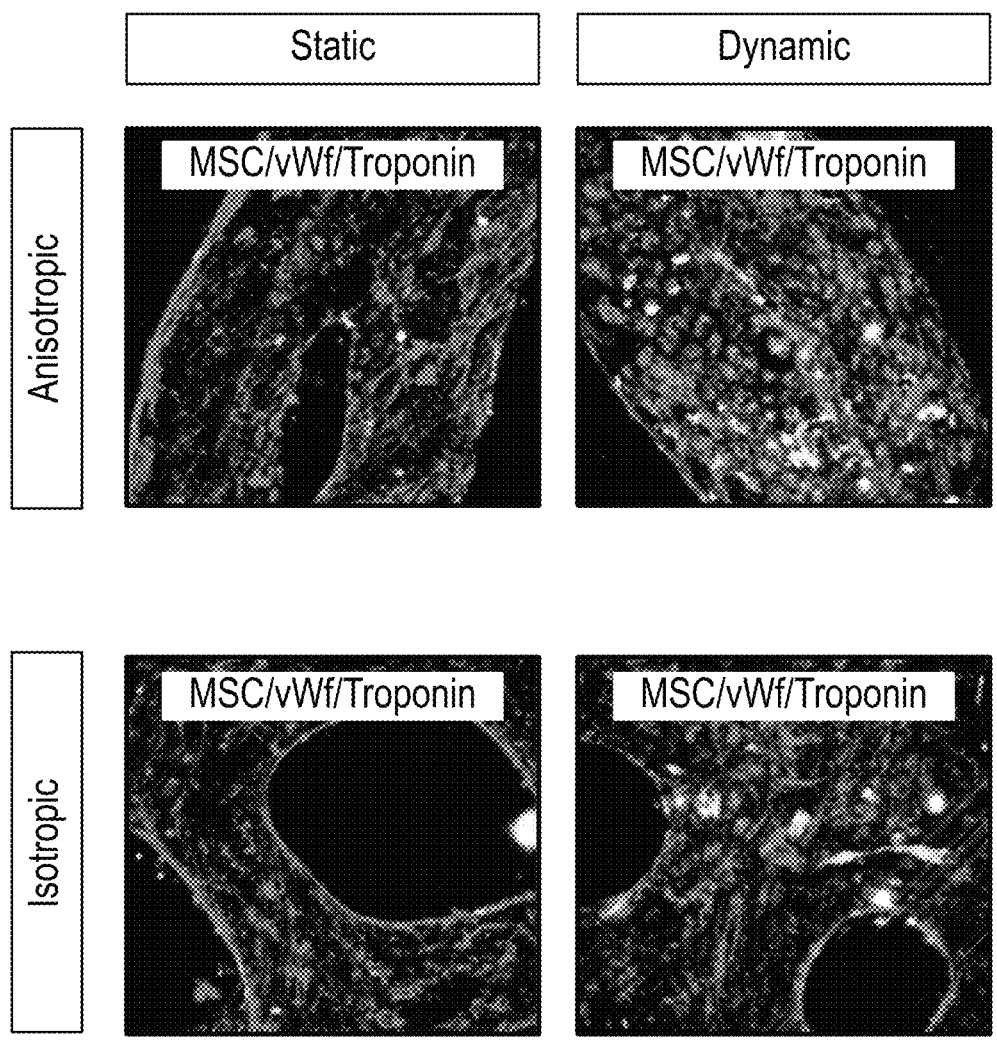
FIG. 6B illustrates cell immunostaining for mesenchymal stem cells (MSC), Von Willebrand factor (vWf), and Troponin for a 7-day post-perfusion culture.
Figure 7A:
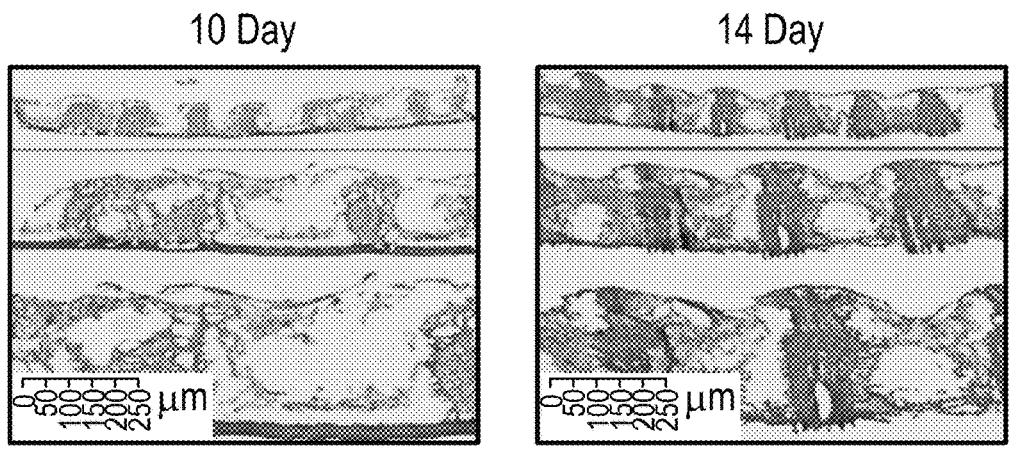
FIGS. 7A-7C illustrate a pathology analysis using Haemotoxylin and Eosin (H&E) staining and immunostaining.
Figure 7B:
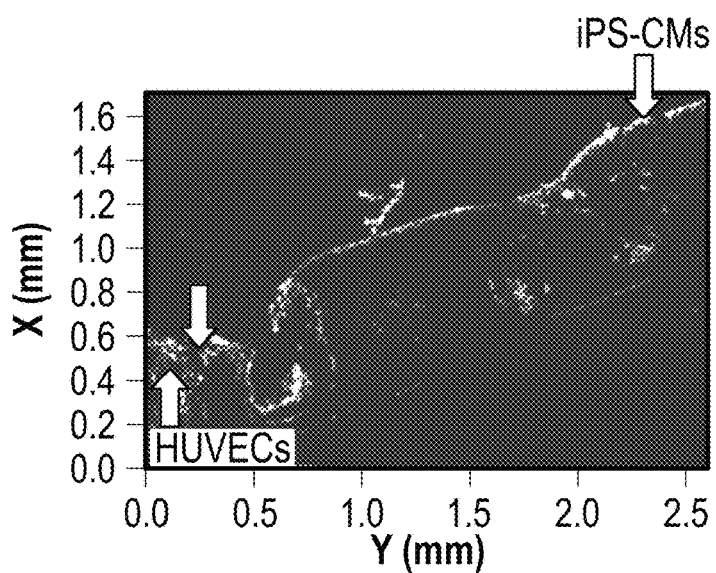
Figure 7C:
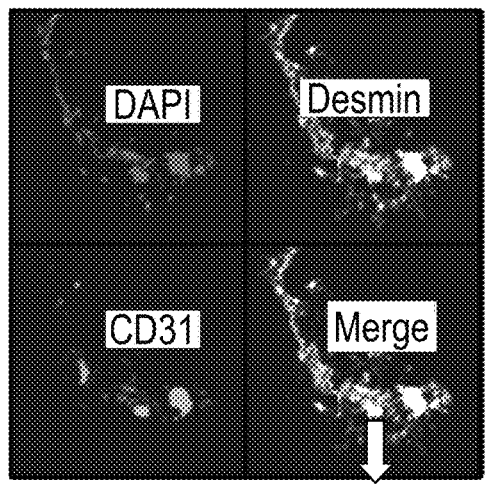
Figure 8A:
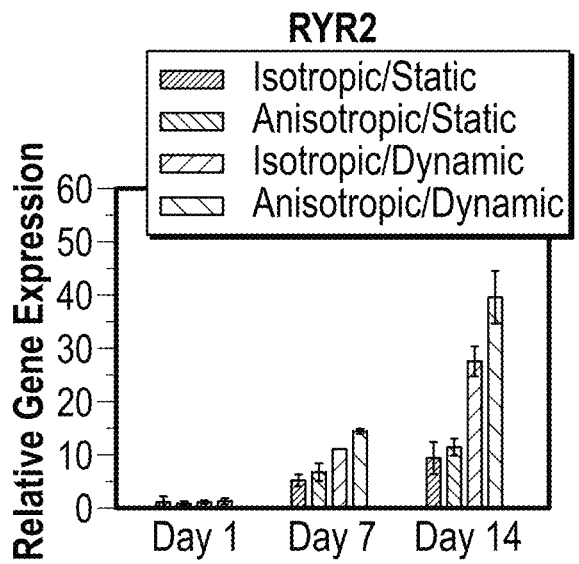
FIGS. 8A-8D are charts illustrating data for a gene expression analysis for an in vitro study of the cardiac patch disclosed herein.
Figure 8B:
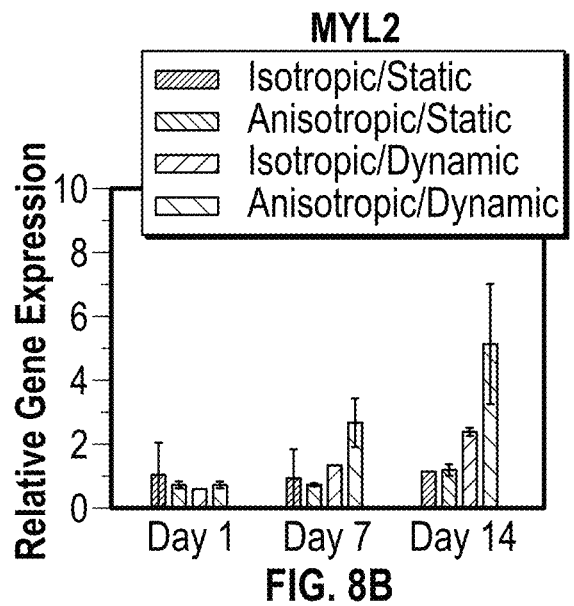
Figure 8C:
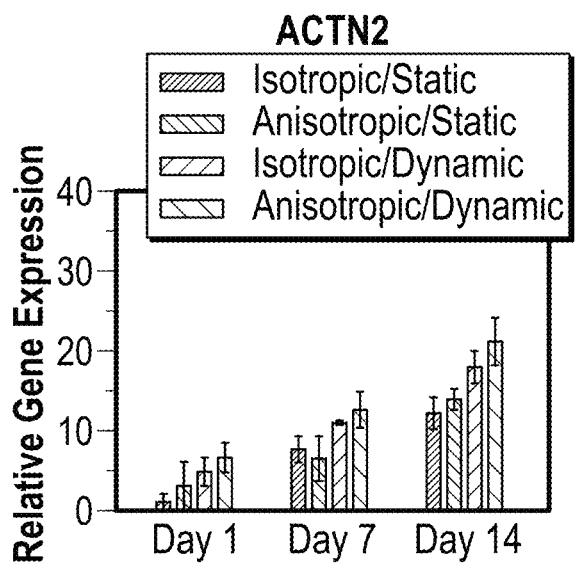
Figure 8D:
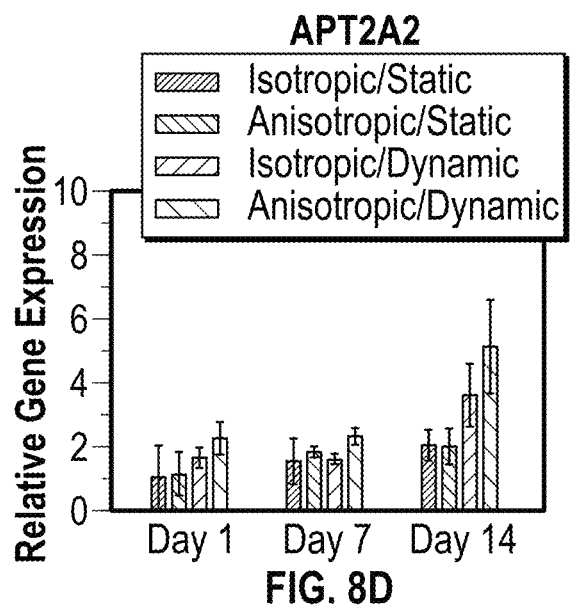
Figure 9A:
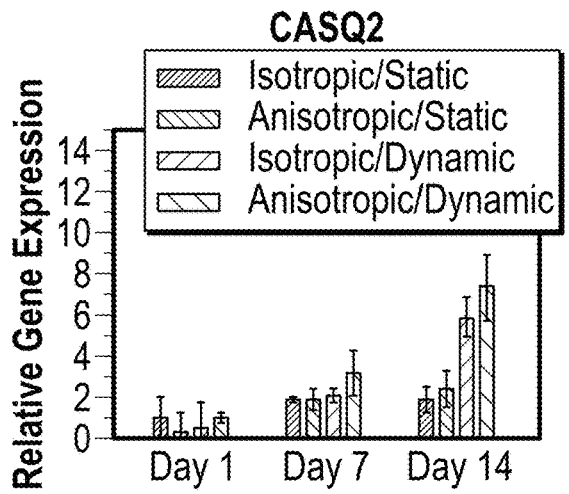
FIGS. 9A-9F are charts illustrating data for a gene expression analysis for an in vitro study of the cardiac patch disclosed herein.
Figure 9B:
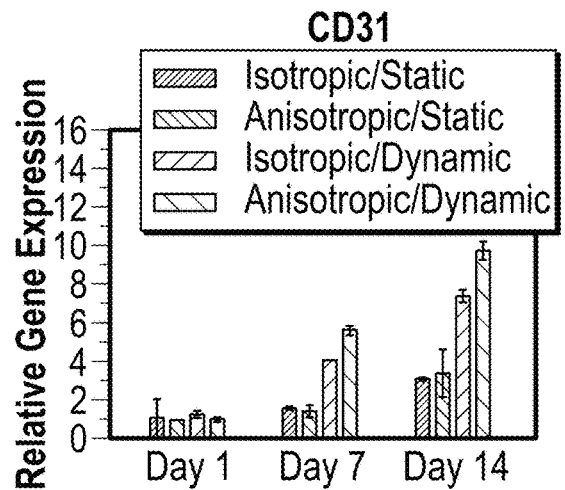
Figure 9C:
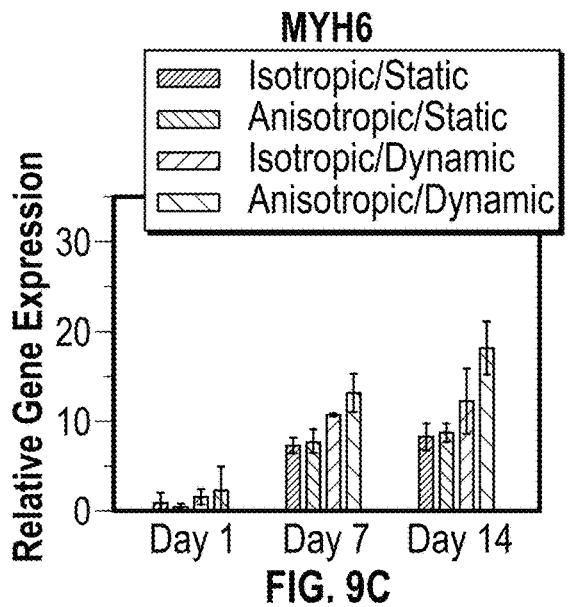
Figure 9D:
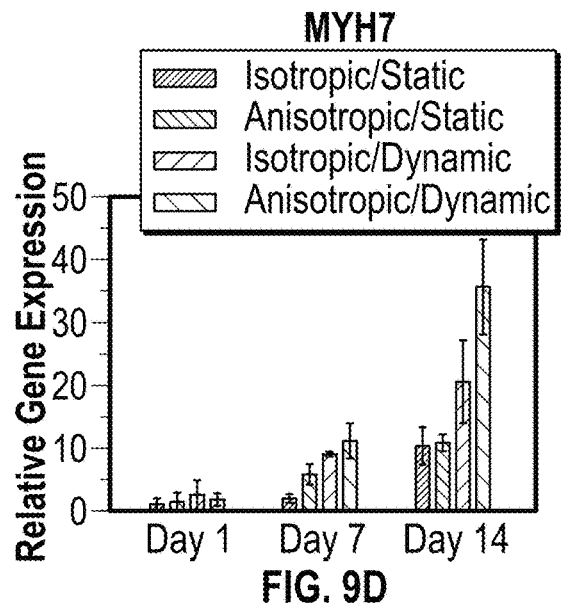
Figure 9E:
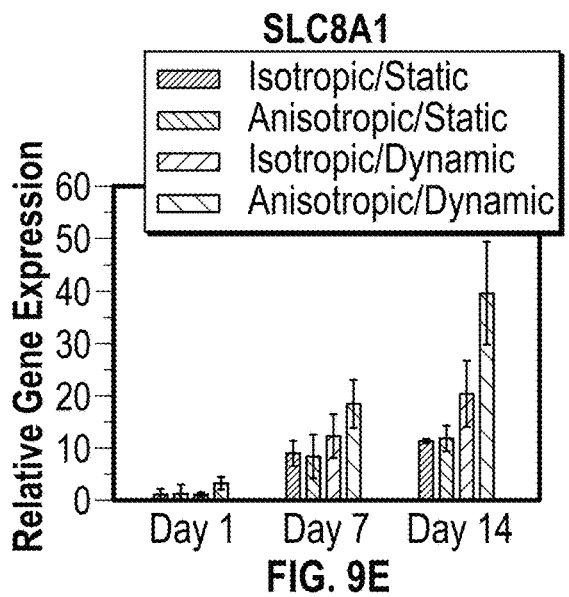
Figure 9F:
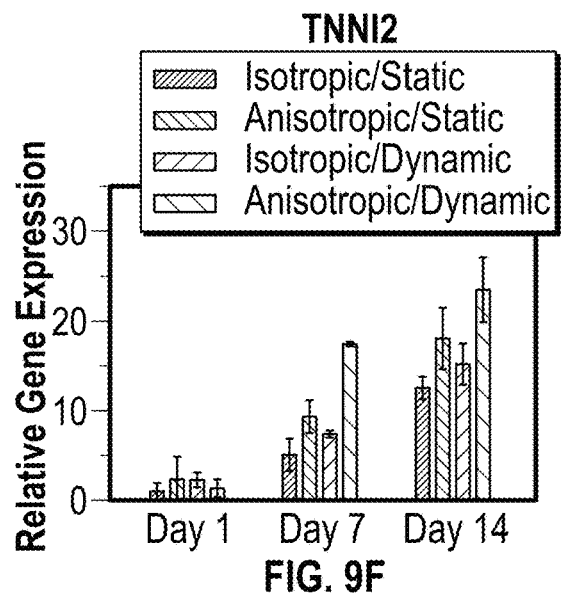
Figure 10A:
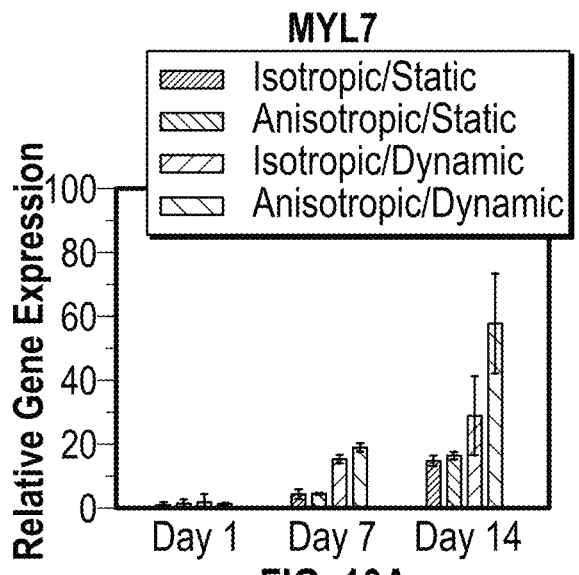
FIGS. 10A-10D are charts illustrating data for a gene expression analysis for an in vitro study of the cardiac patch disclosed herein.
Figure 10B:
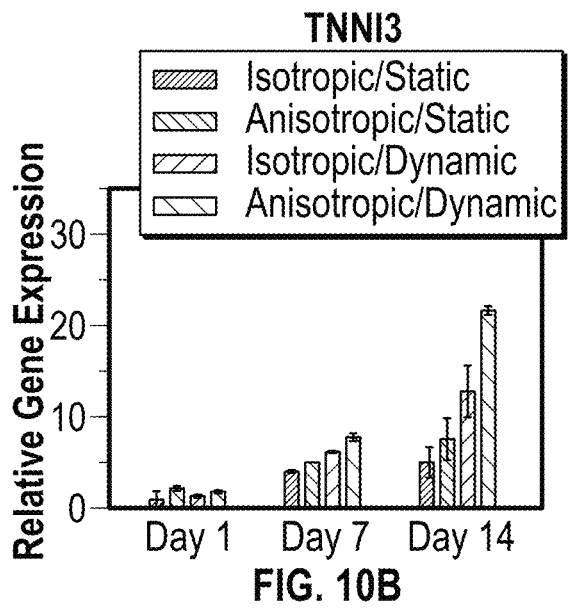
Figure 10C:
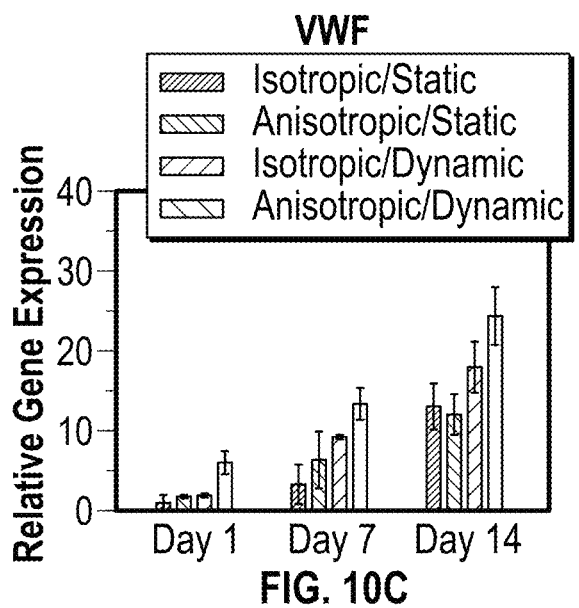
Figure 10D:
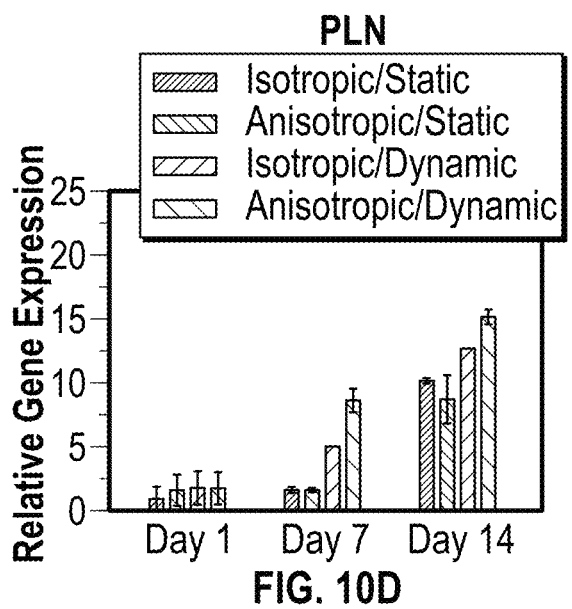

In FIGS. 6A and 6B, the effects of perfusion culture are shown with cell immunostaining for MSC, Von Willebrand factor (vWf), and Troponin. As shown in FIG. 6A, immunostaining was carried out for both anisotropic and isotropic cardiac patches showing first day post-cells seeding, before perfusion culture. FIG. 6B shows day 7 post-perfusion culture for both anisotropic and isotropic cardiac patches. The results demonstrate that HUVECs have a higher angiogenesis under the perfusion culture. FIGS. 7A-7C illustrate a pathology analysis. FIG. 7A shows cross-sectional images of the cardiac patch at 10 day and 14 day culture using Haemotoxylin and Eosin (H&E) staining, and FIG. 7B shows immunostaining of the cross-sections in FIG. 7A, using the cell ratio of 1:2:4 to show HUVECS and iPS-CMs, and FIG. 7C shows immunostaining with DAPI, Desmin, CD31, and a MERGE. These results again demonstrate that HUVECs have a higher angiogenesis under the perfusion culture.

In FIGS. 8A-8D, 9A-9F, and 10A-10D a gene expression analysis was conducted for static versus perfusion culture. The gene expression of cardiac patches with different structure was analyzed under both dynamic and static culture condition by real-time quantitative reverse transcription polymerase chain reaction (RT-PCR) assay. The cardiac tissue related genes including ryanodine receptor 2 (RYR2), myosin light chain 2 (MYL2), α-actinin 2 (ACTN2), SERCA 2α (AP2A2), calsequestrin 2 (CASQ2), platelet endothelial cell adhesion molecule-1 (CD31), myosin heavy chain 6 (MYH6), myosin heavy chain 7 (MYH7), sodium/calcium exchanger 1 (SCC8A1), cardiac Tropnin T (TNNT2), cardiac Tropnin I (TNNI3), myosin light chain 7 (MYL7), vWF, and phospholamban (PLN) were detected. The selected genes are typical functional markers for cardiomyogenesis, and angiogenesis evaluation. The results of FIGS. 8A-8D, 9A-9F, and 10A-10D indicate combining anisotropic structure and perfusion culture can greatly improve the cardiomyogenesis and angiogenesis in 3D bioprinted patches by undergoing contractile force associated with hemodynamics.

In Vivo—Mice Study (Normal NSG Mouse Heart)

Figure 11:
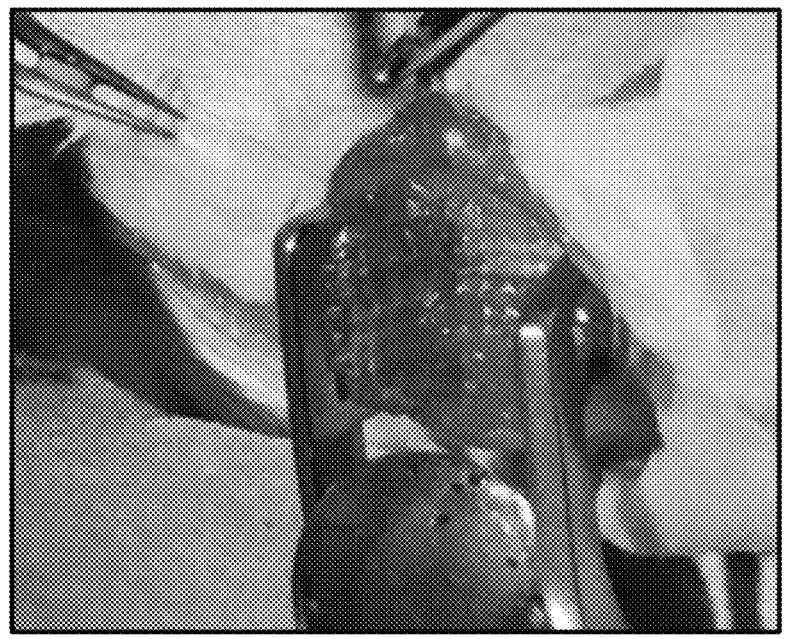
FIG. 11 illustrates the development of cellularized patch in NSG mice, involved in vivo survival and tissue remodeling.
Figure 11:
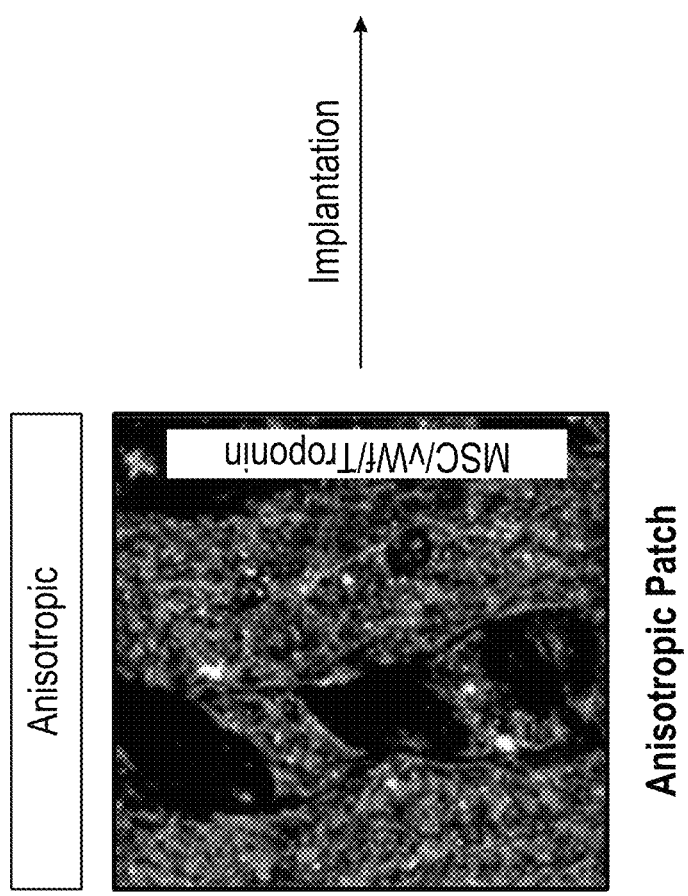

FIG. 11 shows the development of cellularized patch in NSG mice, involving in vivo survival and tissue remodeling (Normal, electric burning injury, and MI) in NSG mice. As shown in FIG. 11, an anisotropic cardiac patch (left side) may be implanted NSG (NOD-SCID IL-2 receptor gamma null) mice (right side). For the in vivo studies, three different models (normal, electric burning, and MI) were chosen to investigate the cell viability, tissue remodeling as well as regeneration.

Figure 12A:
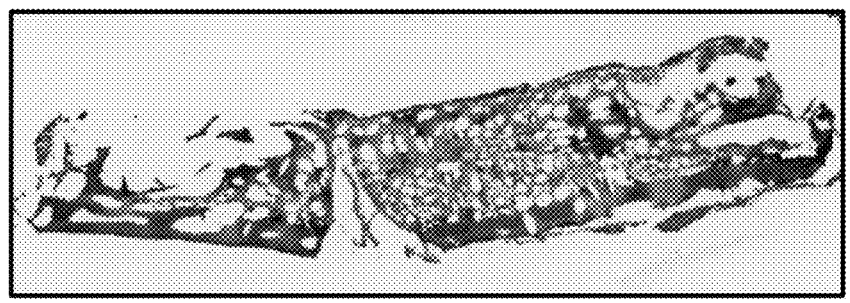
FIGS. 12A-12C provide H&E staining of cross-sectional images of a cardiac patch on a NSG mouse (Normal) heart 3 days post implantation.
Figure 12B:
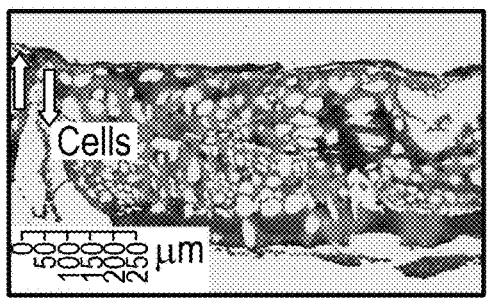
Figure 12C:
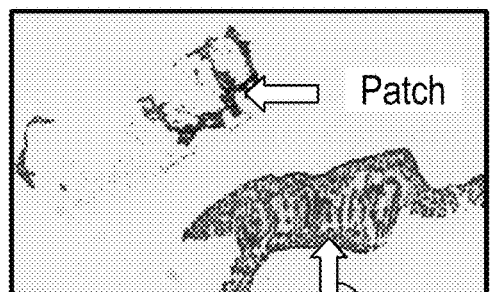
Figure 12D:
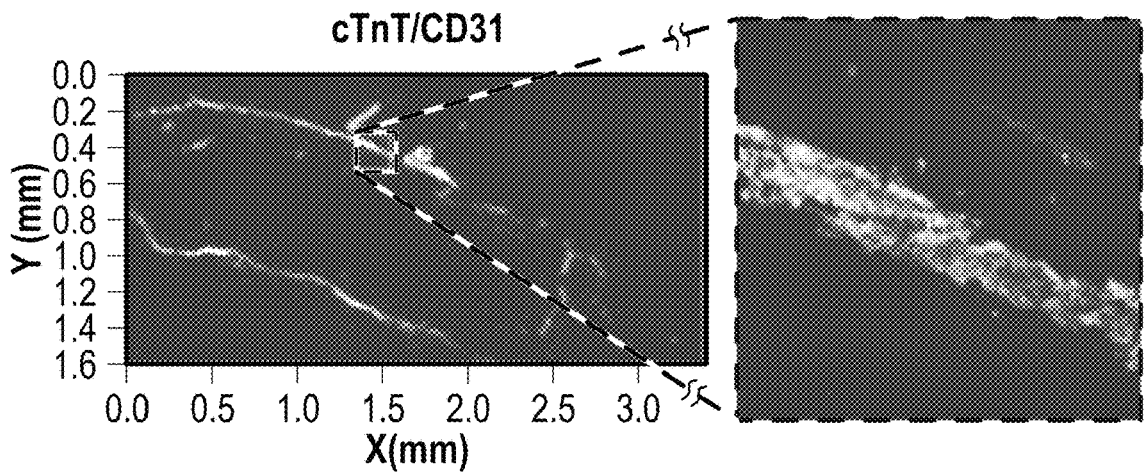
FIG. 12D illustrates immunostaining with cTnT/CD31 a cardiac patch on a NSG mouse (Normal) heart 3 days post implantation.
Figure 12E:
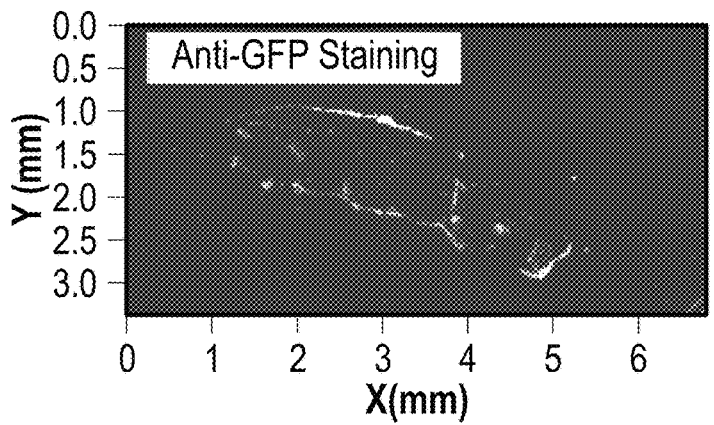
FIG. 12E illustrates iPS-CM identification with using Anti-GFP (Green Fluorescent Protein) a cardiac patch on a NSG mouse (Normal) heart 3 days post implantation.

Illustrated in FIGS. 12A-12C, are H&E staining of cross-sectional images of the cardiac patch, and further shown in FIG. 12D is immunostaining with cTnT/CD31, and in FIG. 12E iPS-CM identification using Anti-GFP (Green Fluorescent Protein) staining. After 3 days of implantation, the cells on the cardiac patches had a high viability in the heart area of the mice. Additionally, the immunostaining data also confirmed the cardiomyogenesis and angiogenesis of the implanted patches.

Figure 13A:
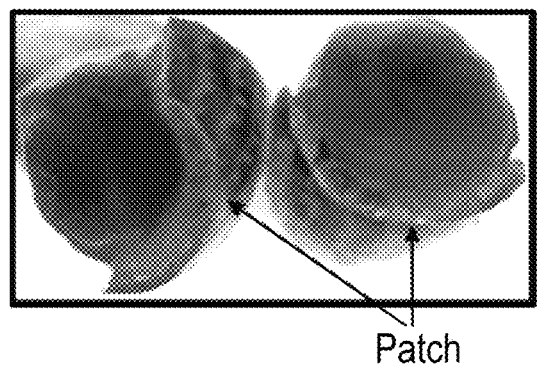
FIG. 13A shows an image of a cardiac patch on a NSG mouse (Normal) heart 1 week after implantation.
Figure 13B:
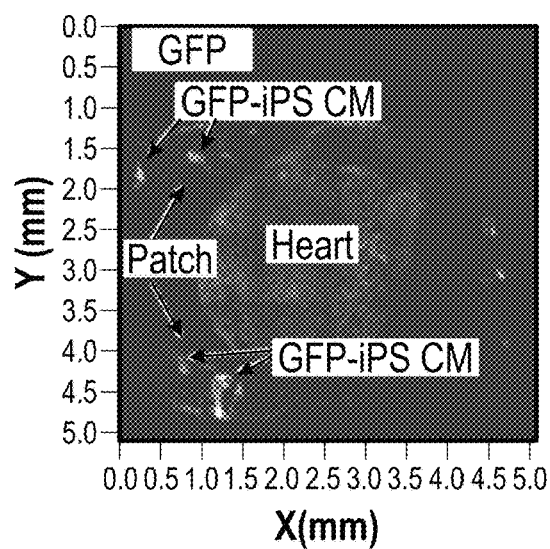
FIG. 13B illustrates GFP staining of a cardiac patch on a NSG mice (Normal) heart 1 week after implantation.
Figures 13C, 13D:
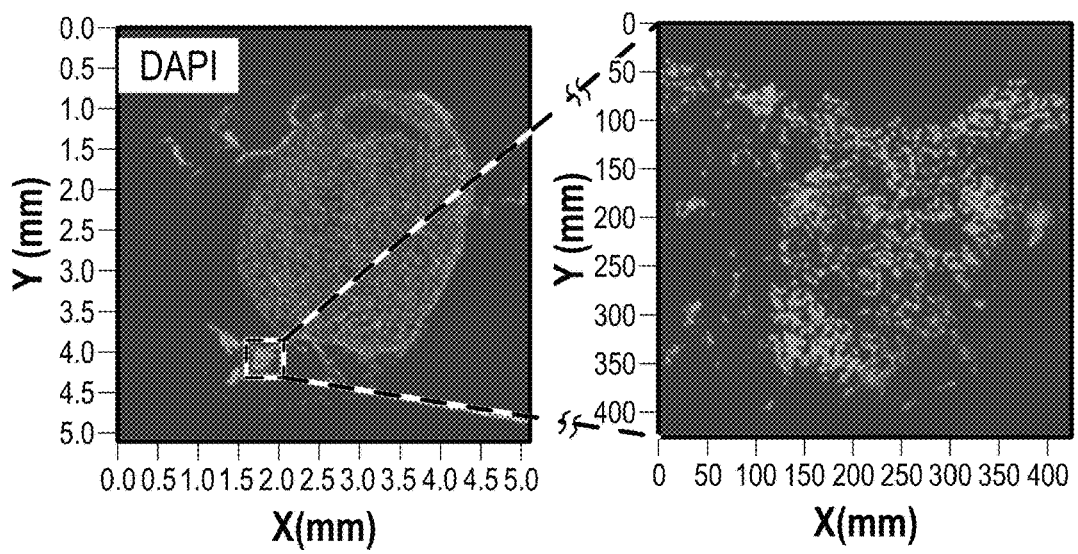
FIGS. 13C-13D illustrate DAPI staining for a cardiac patch on a NSG mice (Normal) heart 1 week after implantation.

FIG. 13A shows an image of the patch on the NSG mice (Normal) heart 1 week after implantation. FIG. 13B illustrates GFP staining and FIGS. 13C-13D illustrate DAPI staining. FIG. 13E shows H&E staining of the cardiac patch, and FIGS. 13F-13H show immunostaining with cTnT/CD31.

Figure 14E:
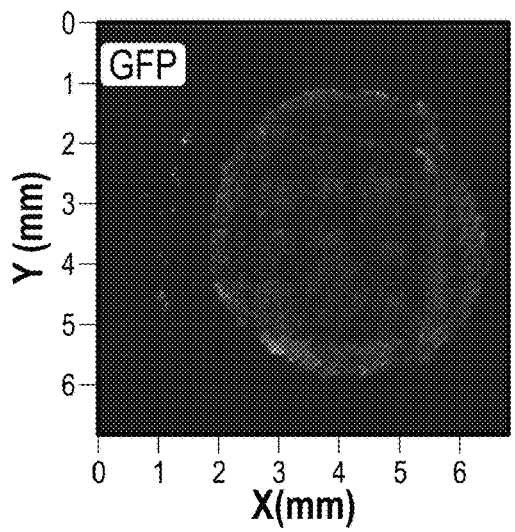
Figure 14F:
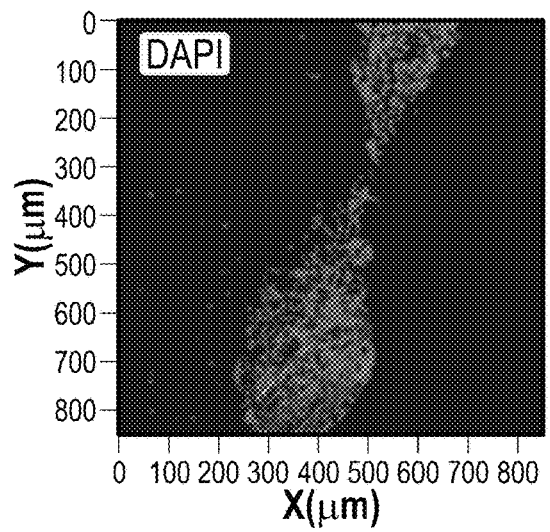
FIGS. 14F and 14G illustrate DAPI staining of a cardiac patch on a NSG mouse (Normal) heart 3 weeks after implantation
Figure 14G:
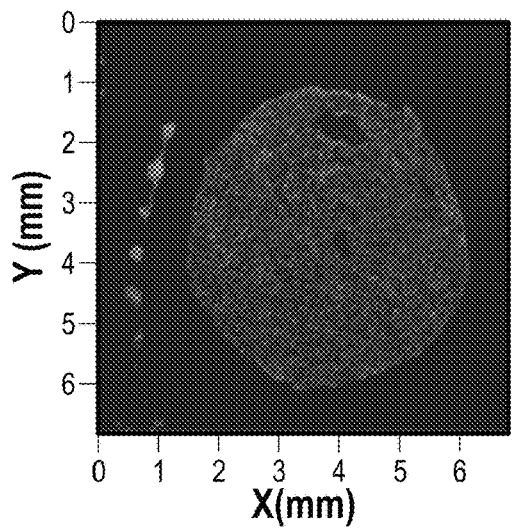
Figure 14H:
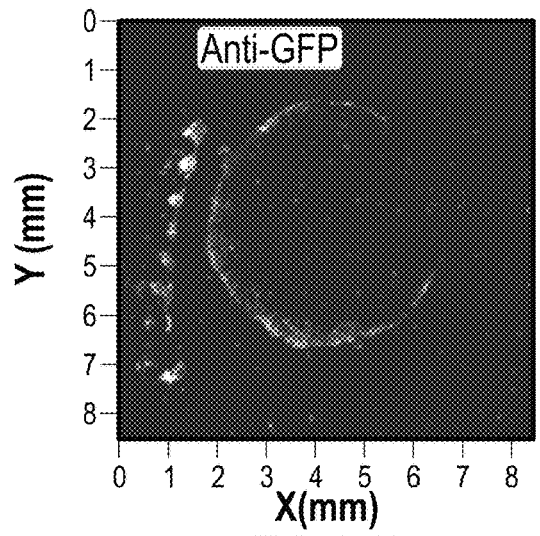
FIG. 14H illustrates anti-GFP staining of a cardiac patch on a NSG mouse (Normal) heart 3 weeks after implantation
Figure 14I:
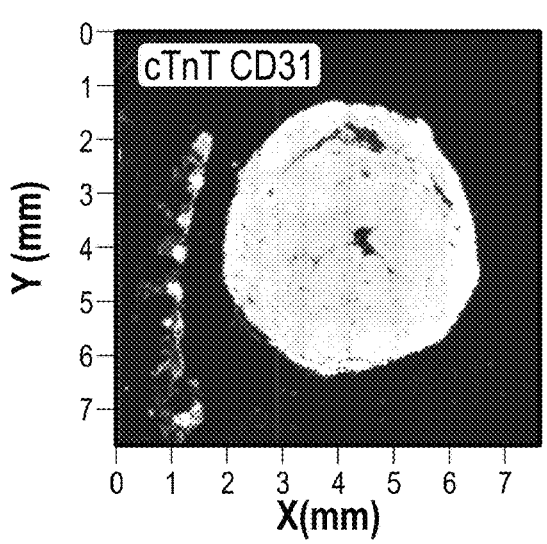
FIGS. 14I and 14J illustrate CTnT/CD31 staining of a cardiac patch on a NSG mouse (Normal) heart 3 weeks after implantation.
Figure 14J:
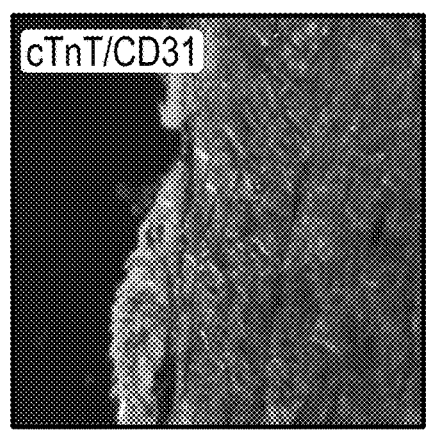

FIGS. 14A-14J show various images and immunostaining of NSG mice (Normal) heart 3 weeks after implantation. FIG. 14A shows an image of the patch on the NSG mice (Normal) heart 3 weeks after implantation. FIGS. 14B and 14C show H&E staining of the cardiac patch. FIGS. 14D-14E show GFP staining, FIGS. 14F and 14G show DAPI staining, FIG. 14H anti-GFP staining, and FIGS. 14I and 14J CTnT/CD31 staining.

FIGS. 15A-15F show imaging and immunostaining of NSG mice (Normal) heart 10 weeks after implantation. In particular, FIG. 15A shows MRI imaging, FIG. 15B an image, and FIG. 15C stereofluorescence of the cardiac patch on the NSG mice (Normal) heart. FIGS. 15D-15E shows cross-sectional images of the cardiac patch with H&E staining. Ten weeks after implantation, the cells on the cardiac patch had high viability and proliferation ability in the heart area of the mice. Additionally, the cardiac function parameters were calculated using (shown in FIG. 15A). The data, including the data provided in FIG. 15F, suggests that the heart function of mice was not affected by implanted patches.

In Vivo—Mice Study (Post-Electrical Burning Injury NSG Mouse Heart)

Figure 16A:
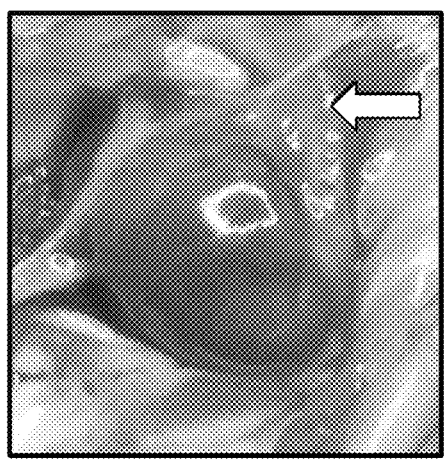
FIGS. 16A-16C illustrates images of a cardiac patch on a NSG mouse heart with Post-electrical burning injury.
Figure 16B:
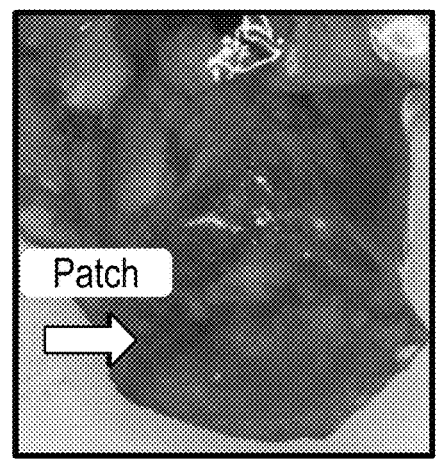
Figure 16C:
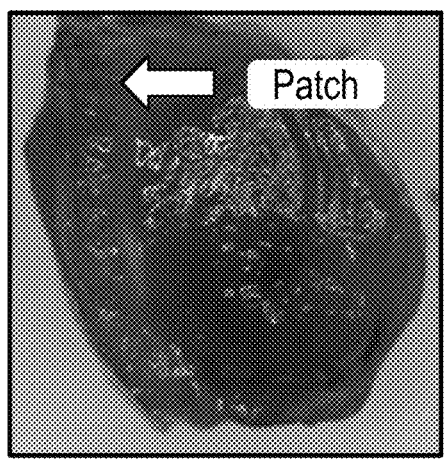
Figure 16D:
FIG. 16D illustrates H&E staining of a cardiac patch on a NSG mouse heart with Post-electrical burning injury.
Figure 16E:
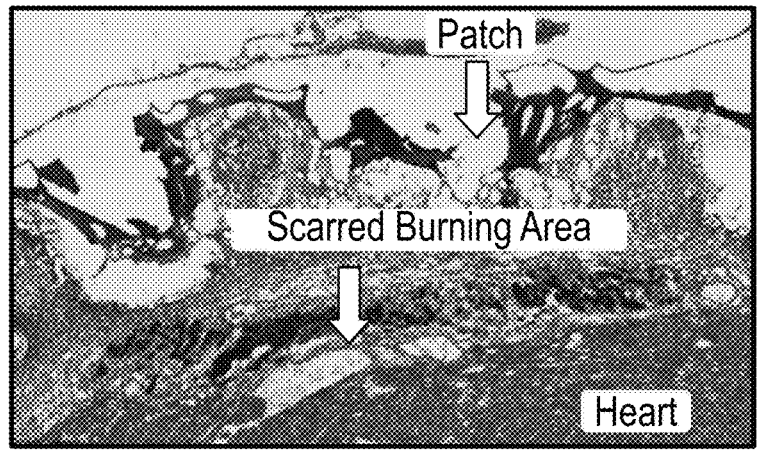
FIG. 16E showing a close up image of a cardiac patch and the scarred burning area of the heart of an NSG mouse 6 weeks after implantation.

FIGS. 16A-16E show images and staining regarding myocardial remodeling at 6 weeks after implantation of a cardiac patch on NSG mice (post-electrical burning injury). FIGS. 16A-16C show images of the cardiac patch on the mouse heart. FIGS. 16D and 16E shows H&E staining, with FIG. 16E showing a close up image of the patch and the scarred burning area.

Figure 17A:
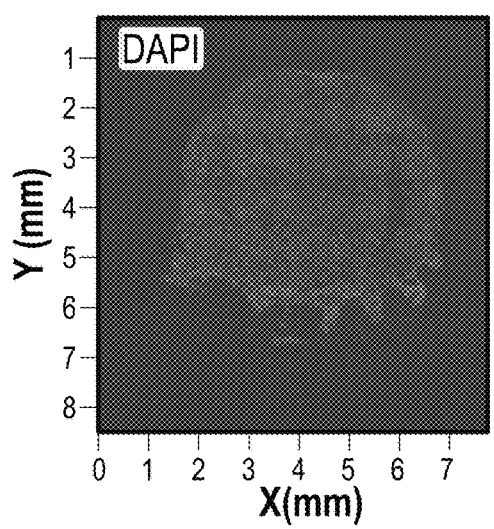
FIGS. 17A-17E illustrate staining showing implanted cells integrated with NSG mouse myocardium 6 weeks after implantation.
Figure 17B:
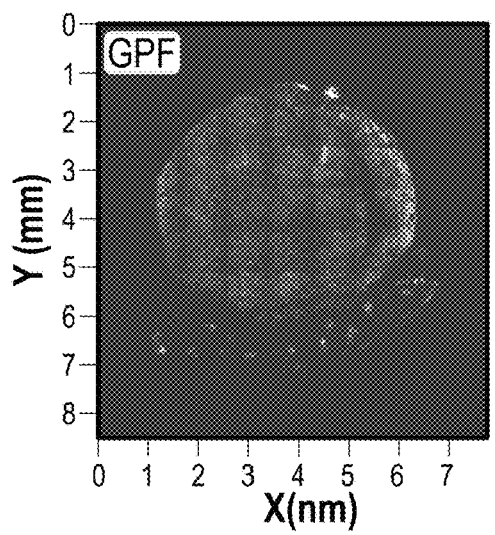
Figure 17C:
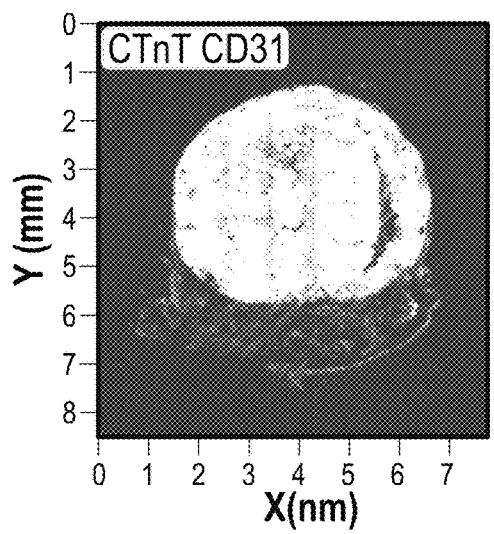
Figure 17D:
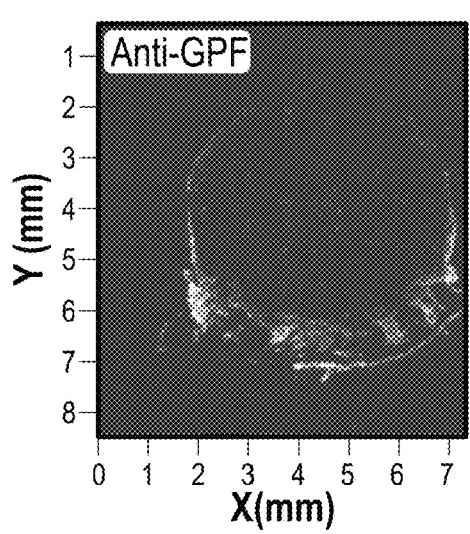
Figure 17E:
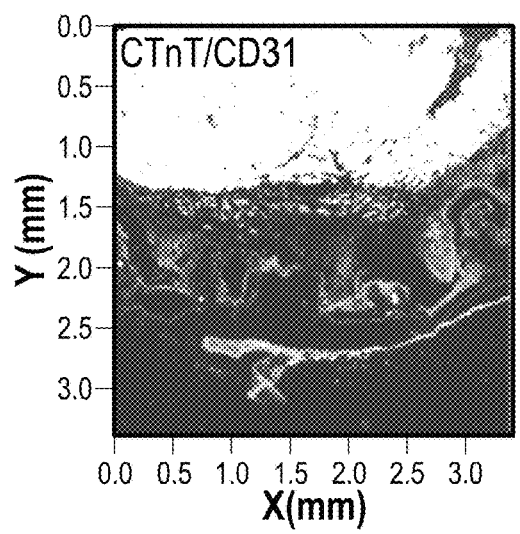

FIGS. 17A-17E include images showing that the implanted iPSC-cardiomyocytes are viable, and integrated with mouse myocardium as time increases. FIG. 17A shows DAPI staining, FIG. 17B GFP staining, FIG. 17C CTnT/CD31 staining, FIG. 17D Anti-GFP staining, and FIG. 17E as close up view of CTnT/CD31 staining.

FIGS. 18A and 18B show MRI images the NSG mouse heart and patch, and FIG. 18C provides data for the same, for myocardial remodeling at 6 weeks post implantation for the heart with the electrical burn injury. The images and data show no ventricular enlargement or hypertrophy, with left and right ventrical size and the myocardial mass in the normal range, which are similar to those data in normal model.

Figure 20A:
FIGS. 20A-20F illustrate images and staining regarding myocardial remodeling at 10 weeks after implantation of a cardiac patch on NSG mice (post-electrical burning injury).
Figure 20B:
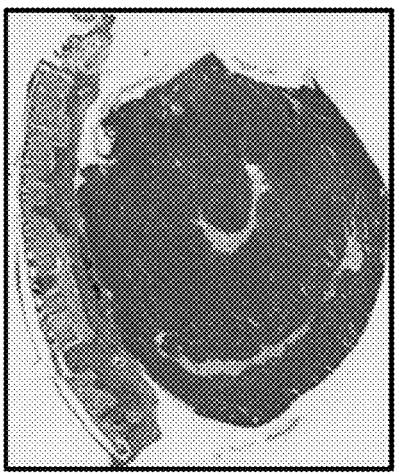
Figure 20C:
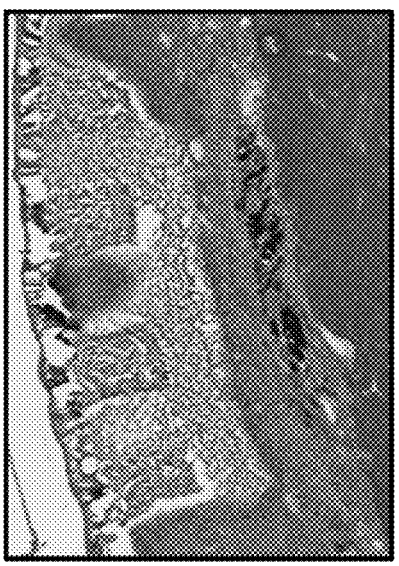
Figure 20D:
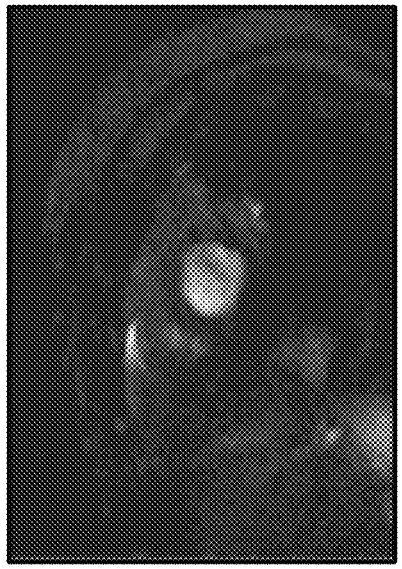
Figure 20E:
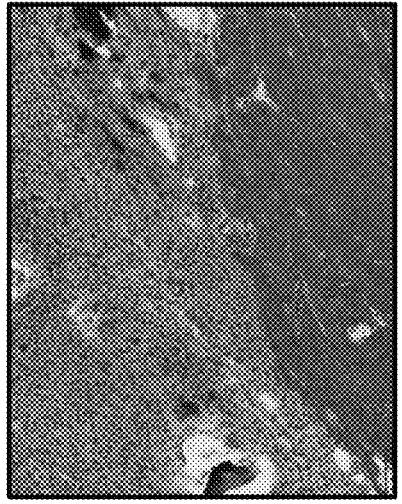
Figure 20F:
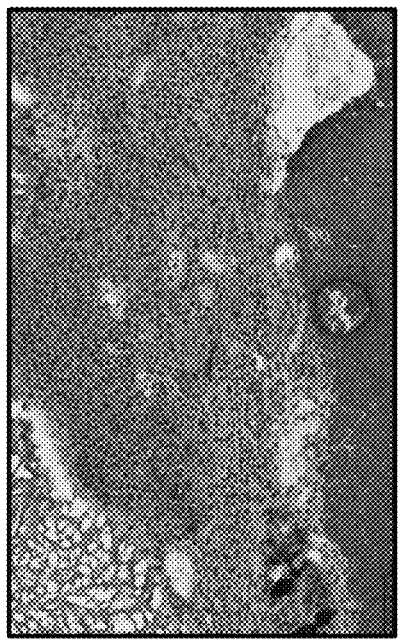

FIGS. 19A-19F show images regarding myocardial remodeling at 10 weeks after implantation of a cardiac patch on NSG mice (post-electrical burning injury). FIGS. 19A-19F show MRI imaging, with data shown in FIG. 19G for heart function. The MRI imaging and data show that 10 weeks after implantation, here is no difference in cardiac function. FIGS. 20A-20F show images and staining regarding myocardial remodeling at 10 weeks after implantation of a cardiac patch on NSG mice (post-electrical burning injury). FIG. 20A shows imaging and FIGS. 20B-20C show H&E staining for remodeling of the injured area. FIG. 20D shows imaging and FIGS. 20E-20F show H&E staining for angiogenesis in the remodeling area.

In Vivo—Mice Study (MI in NSG Mouse Heart)

Figure 21C:
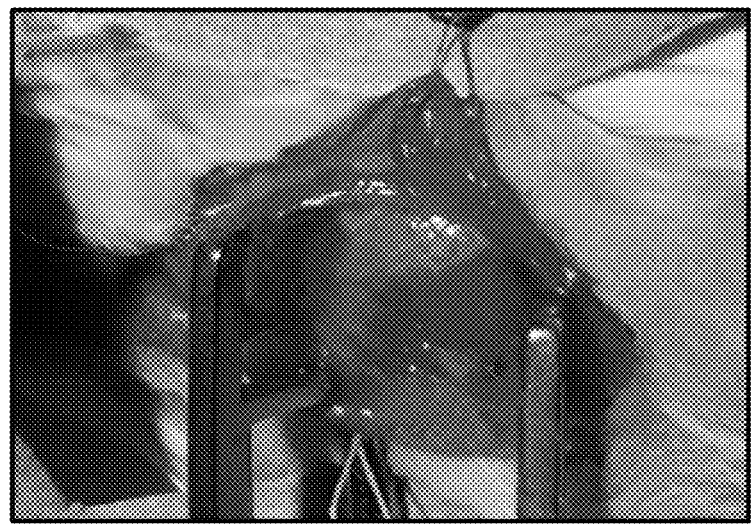
FIGS. 21A-21C illustrates a cardiac patch implanted on a NSG mouse heart with MI.
Figure 21B:
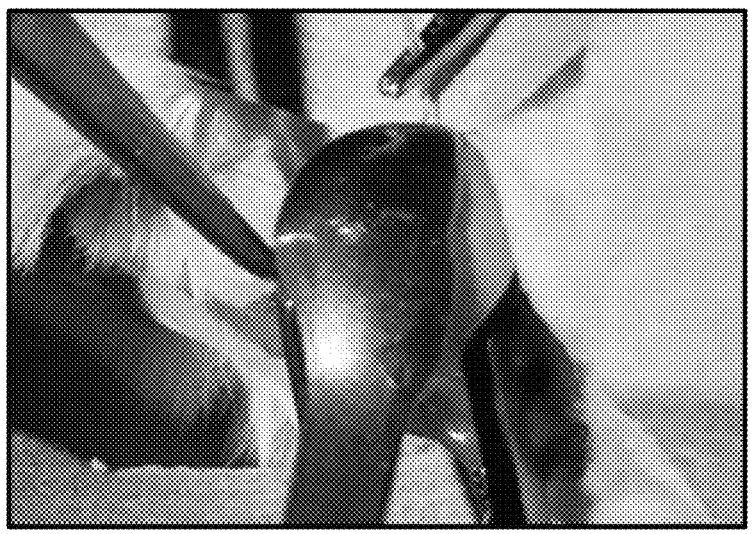
Figure 21A:
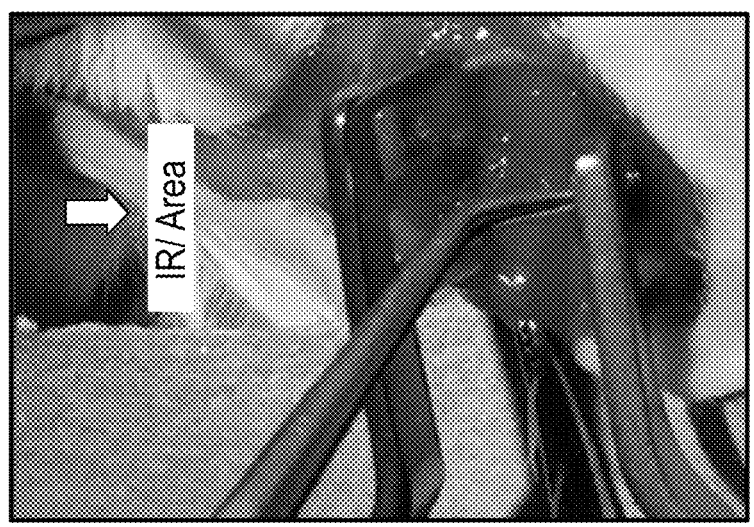

In order to mimic human MI disease, the cardiac patch was implanted onto cardiac Ischemia/Reperfusion (IR) area in NSG mouse as illustrated in FIGS. 21A-21C. FIG. 22A shows H&E staining of the cardiac patch and heart 1 day after implantation, and FIG. 22C shows H&E staining of the cardiac patch and heart 6 weeks after implantation. FIG. 22B shows a picture of the heart with the patch thereon. The H&E staining showed that the implanted cardiac patch maintains high cell viability and improved MI.

Figure 23A:
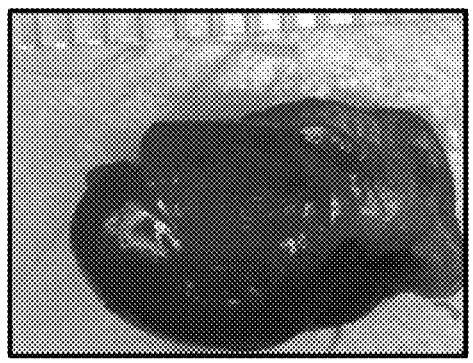
FIG. 23A illustrates a picture of a NSG mouse heart having MI with a cardiac patch thereon 6 weeks after implantation.
Figure 23B:
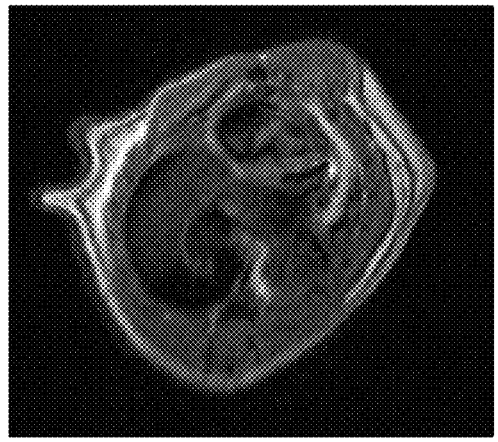
FIGS. 23B-23C illustrate MRI imaging of a cardiac patch on a NSG mouse heart having MI 6 weeks after implantation.
Figure 23C:
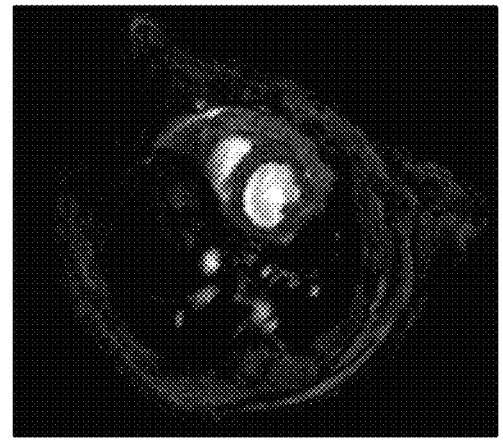
Figure 23D:
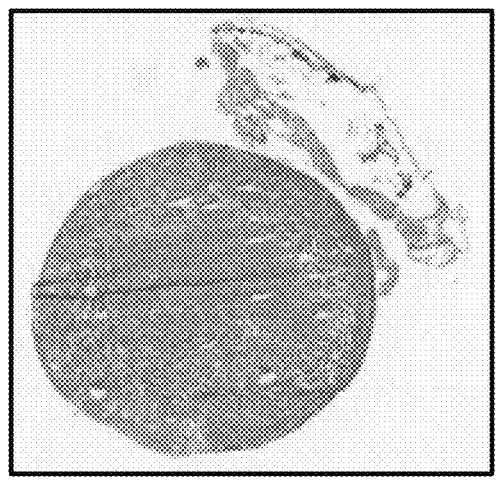
FIGS. 23D-23E H&E staining of a cardiac patch on a NSG mouse heart having MI with a cardiac patch thereon 6 weeks after implantation.
Figure 23E:
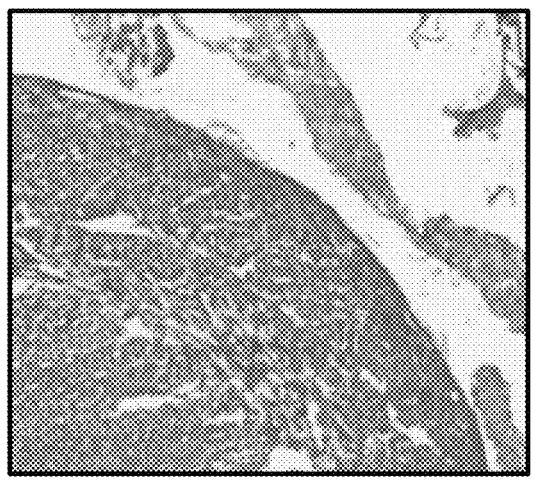
Figures 24A, 24B, 24C, 24D:
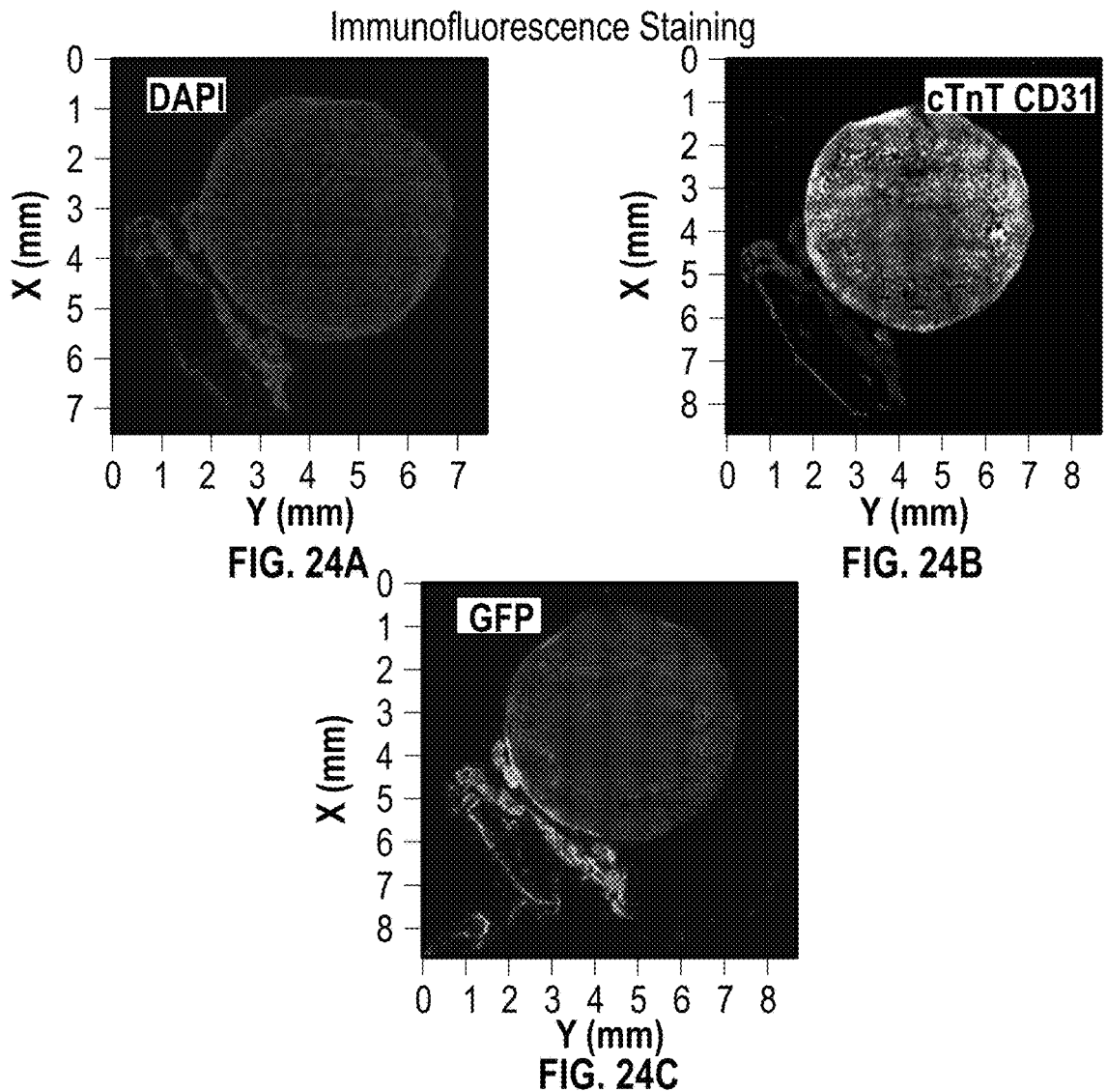
FIGS. 24A-24C illustrate staining of a cardiac patch on a NSG mouse heart having MI 6 weeks after implantation.
FIG. 24D is a chart having data of heart function for a NSG mouse heart having MI at 6 weeks after implantation of a cardiac patch.

FIGS. 23A-23E show imaging and staining for the cardiac patch at 6 weeks implantation for the MI NSG mouse. FIG. 23A again shows the heart with the patch thereon for reference, whereas FIGS. 23B-23C show MRI imaging and FIGS. 23D-23E show H&E staining. At this same time frame (6 weeks after implantation), FIG. 24A illustrates DAPI staining, FIG. 24B cTnT CD31 staining, and FIG. 24C GFP staining. Furthermore, FIG. 24D provides data for heart function at 6 weeks after implantation.

Figure 25A:
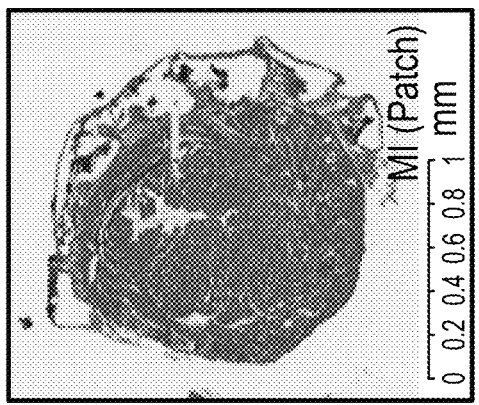
FIGS. 25A-25B show H&E staining of a cardiac patch on a NSG mouse heart having MI 10 weeks after implantation.
Figure 25B:
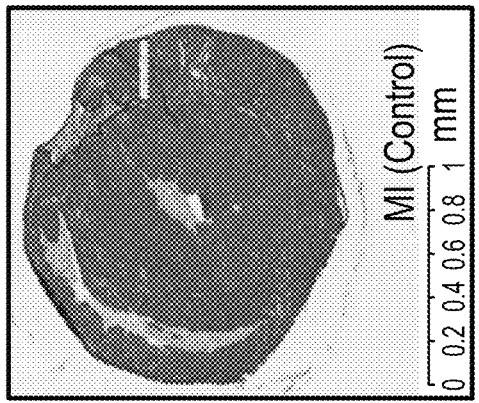
Figure 25C:
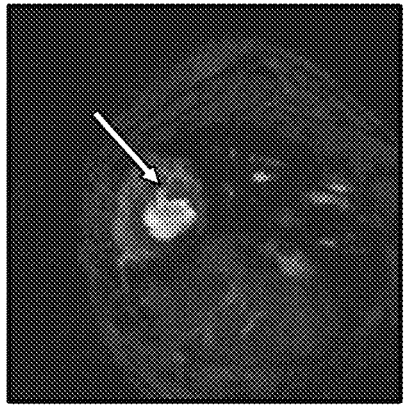
FIGS. 25C-25E show MRI imaging of a cardiac patch on a NSG mouse heart having MI 10 weeks after implantation.
Figure 25D:
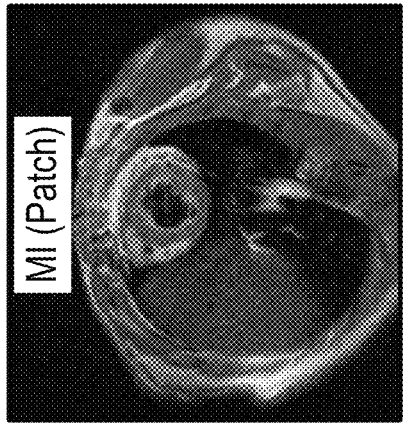
Figure 25E:
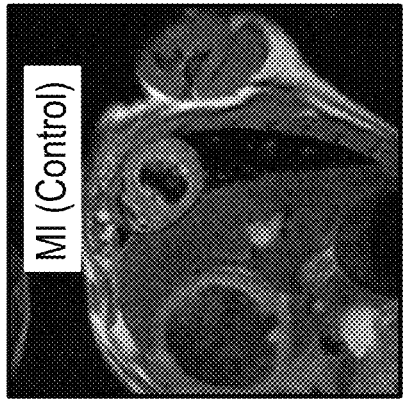

FIGS. 25A-25E show imaging and staining for the cardiac patch at 10 weeks implantation for the MI NSG mouse. FIGS. 25A-25B show H&E staining, FIGS. 25C-25E show MRI imaging. At this same time frame (10 weeks after implantation), FIG. 26A illustrates DAPI staining, FIG. 26B GFP staining, and FIGS. 26C-26D show CTnT/vWf staining. Furthermore, FIG. 26E provides data for heart function at 10 weeks after implantation.

Figure 27A:
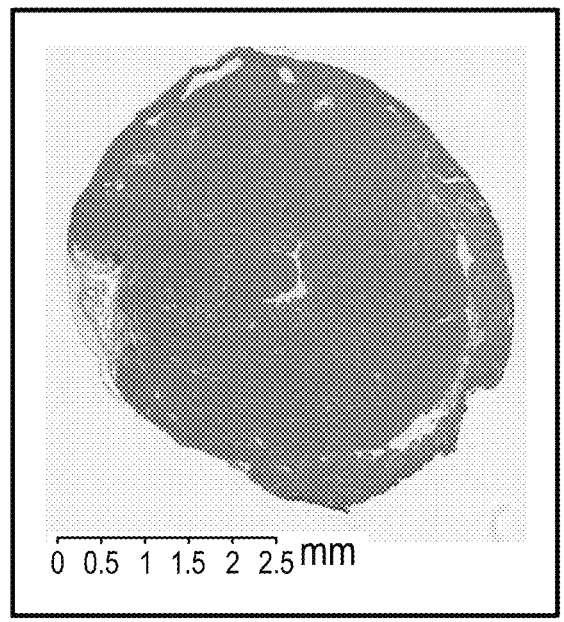
FIG. 27A illustrates a MI heart of an NSG mouse without a patch (control) with H&E staining at 4 months after implantation.
Figure 27B:
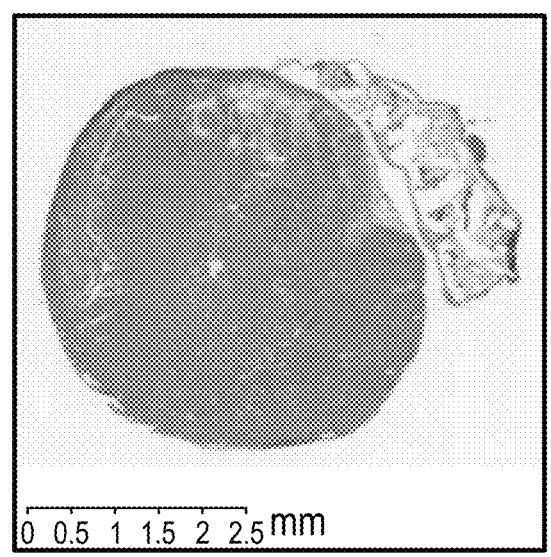
FIG. 27B illustrates a MI heart of an NSG mouse with a cardiac patch with H&E staining at 4 months after implantation.

FIGS. 27A-27E show imaging and staining for the cardiac patch at 4 month implantation for the MI NSG mouse. FIG. 27A shows a MI heart of an NSG mouse without a patch (control) and FIG. 27B shows a MI heart of NSG mouse having a patch with H&E staining. FIGS. 27C and 27E show MRI imaging for the control whereas FIGS. 27D and 27F show imaging for the MI heart of NSG mouse having a patch.

FIGS. 28A-28D show staining for the cardiac patch at 4 month implantation for the MI NSG mouse. FIG. 28A shows DAPI staining, FIG. 28B shows GFP staining, FIGS. 28C-28D CTnT/vWF staining. FIG. 28E shows data for heart function for this time frame.

Figure 29A:
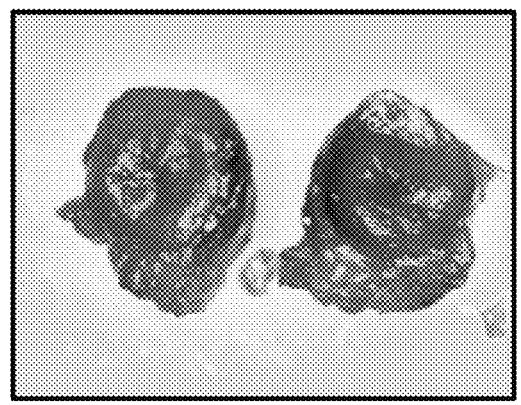
FIG. 29A illustrates an image of a NSG mouse heart having MI with a cardiac patch at 6 month after implantation.
Figure 29B:
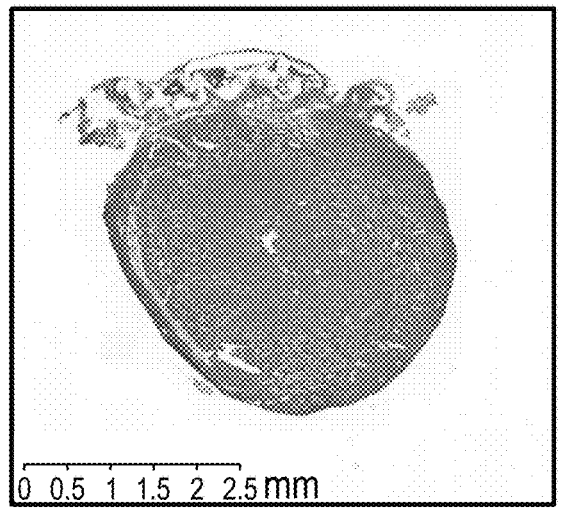
FIGS. 29B and 29C show H&E staining of a NSG mouse heart having MI with a cardiac patch at 6 month after implantation.
Figure 29C:
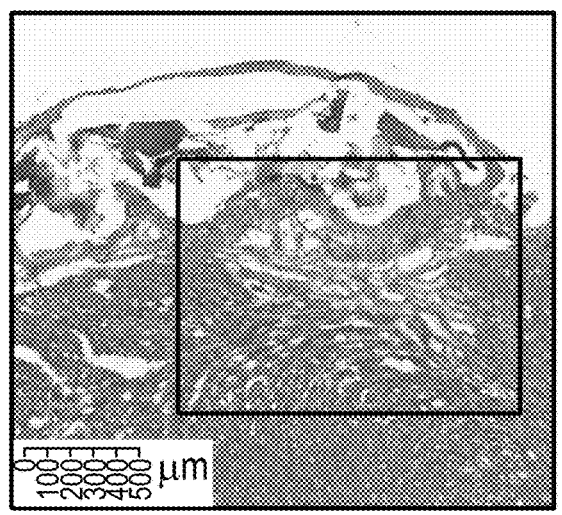
Figure 30A:
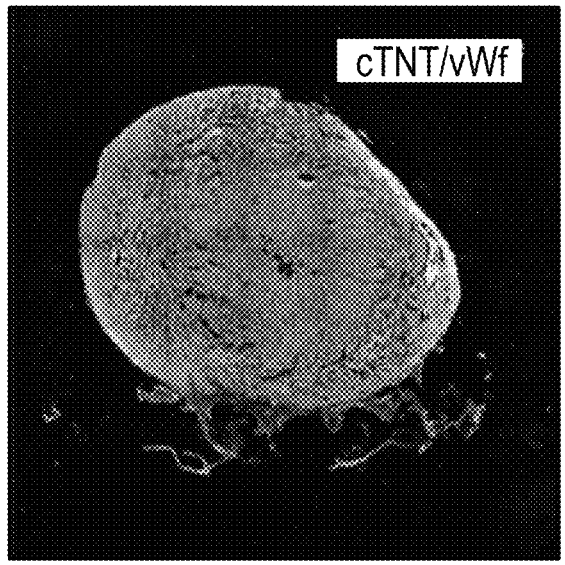
FIGS. 30A-30D illustrate staining for a cardiac patch at 6 month implantation on a NSG mouse heart having MI.
Figure 30B:
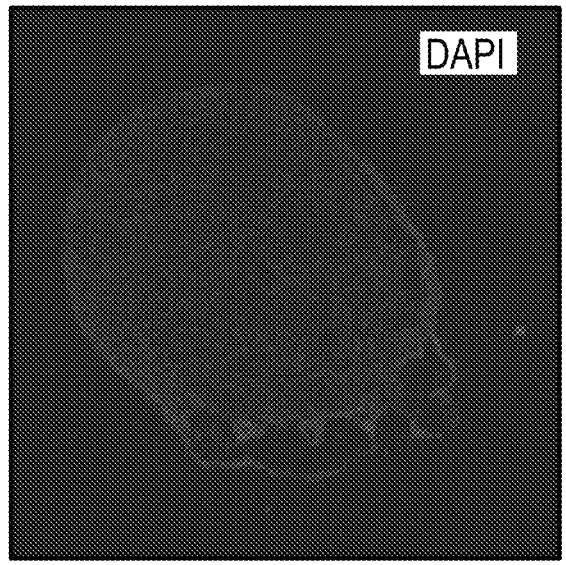
Figure 30C:
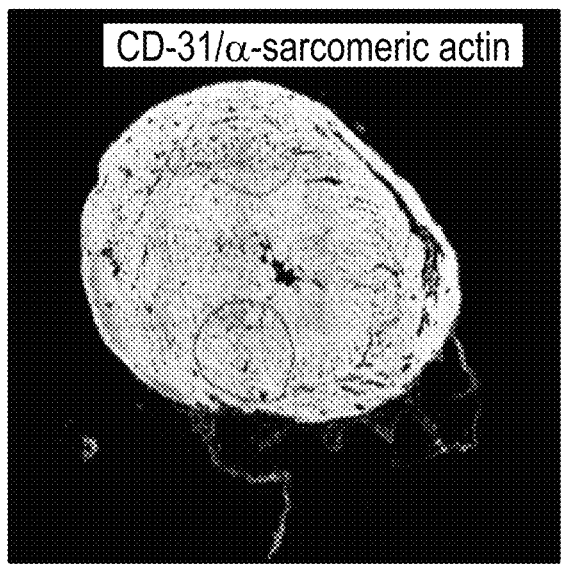
Figure 30D:
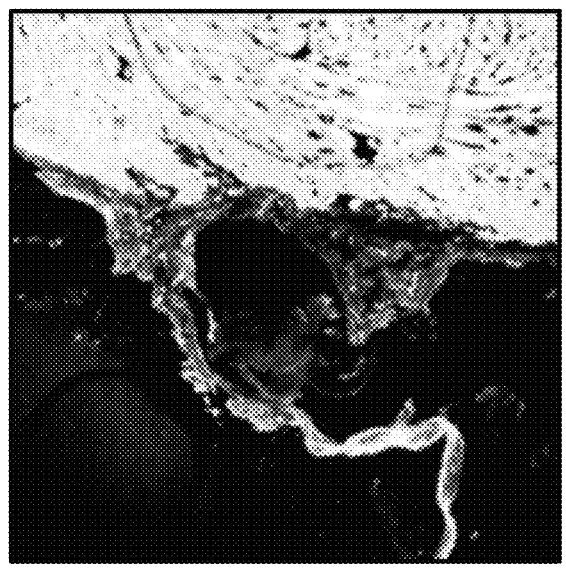

FIG. 29A shows an image of a heart for the cardiac patch at 6 month implantation for the MI NSG mouse. FIGS. 29B and 29C show H&E staining at this time frame and FIG. 30A show cTNT/vWf staining, FIG. 30B shows DAPI staining, FIG. 30C CD31/α-sarcomeric actin and FIG. 30D shows a closeup of the CD31/α-sarcomeric actin staining of FIG. 30C.

Thick Patch Study

The anisotropic and perfusable structure of the cardiac patch disclosed herein permits the use of thicker patches. With thicker patches the human heart may be treated and with more success. The thick patch studies illustrate data for a cardiac patch at 2 mm thick, which is discussed in the following figures.

Figure 31A:
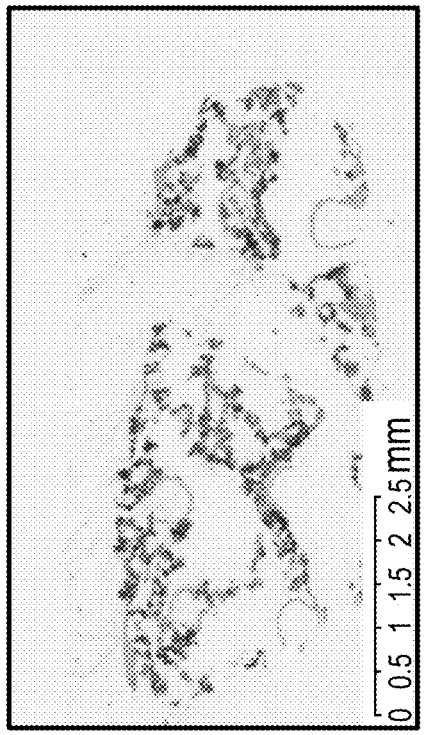
FIGS. 31A-31D illustrate H&E staining dynamic culture and compression for a thick cardiac patch with perfusable vessels which is anisotropic versus one which is isotropic.
Figure 31B:
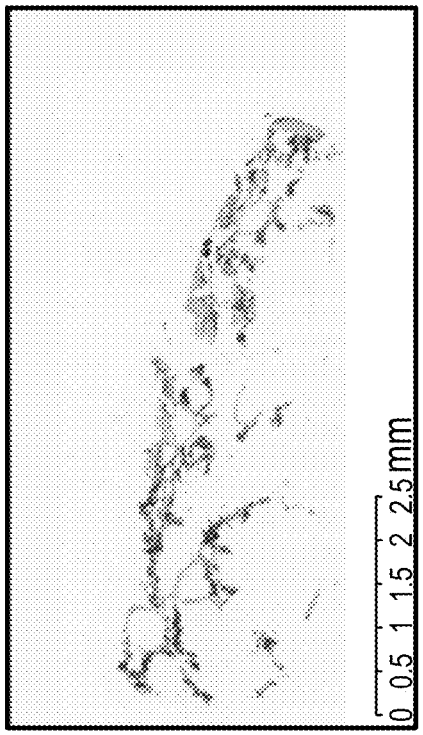
Figure 31C:
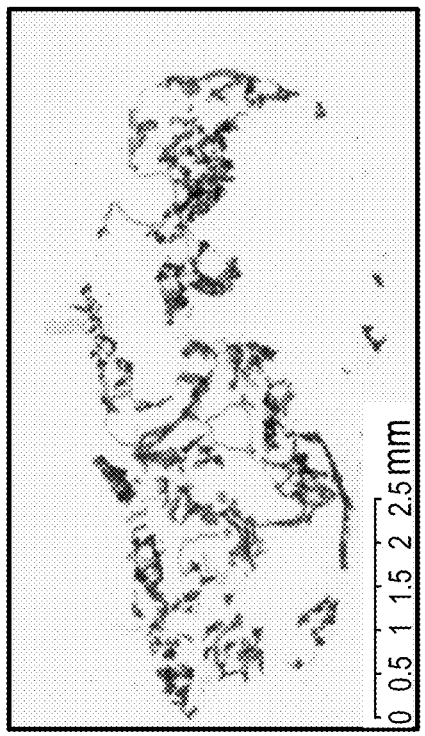
Figure 31D:

FIGS. 31A-31D illustrate H&E staining dynamic culture and compression for a thick cardiac patch with perfusable vessels which is anisotropic versus one which is isotropic. FIG. 31A shows a static isotropic culture as compared to FIG. 31B which shows a static anistopic culture. FIG. 31C shows isotropic dynamic/compression culture as compared to FIG. 31D shows an anisotropic dynamic/compression culture. Furthermore, FIGS. 32A and 32B illustrate H&E staining and FIGS. 32C and 32D show immunostaining of a thick cardiac anisotropic patch.

Figure 33A:
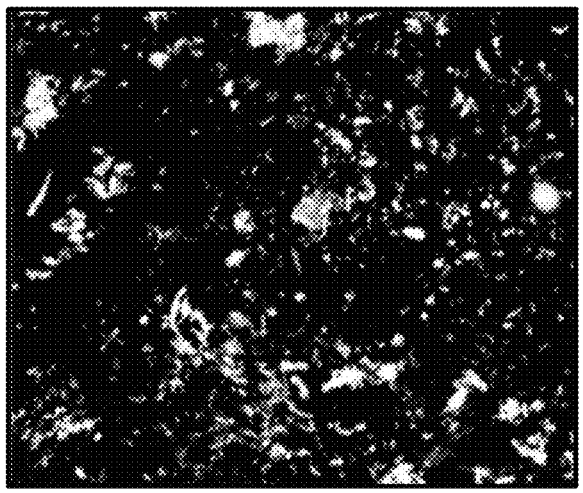
FIGS. 33A-33D illustrate H&E and immunostaining for static and dynamic/compression cultures for thick isotropic and anisotropic cardiac patches.
Figure 33B:
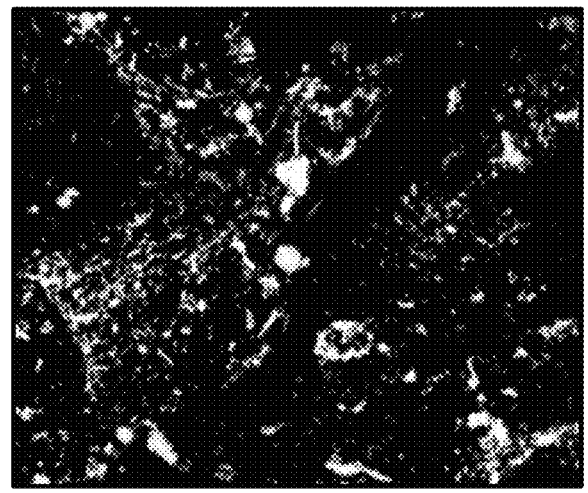
Figure 33C:
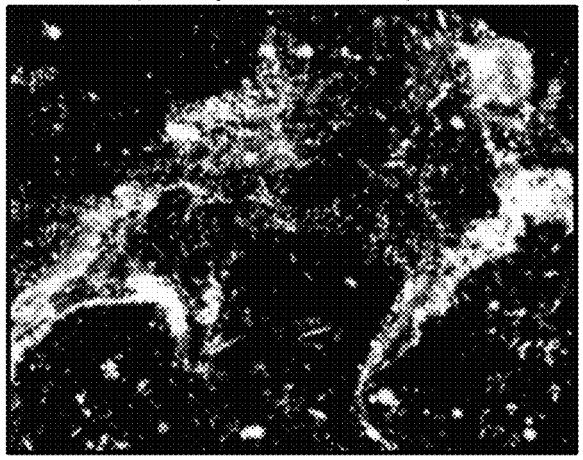
Figure 33D:
Figure 34B:
FIGS. 34A-34D illustrate DAPI staining for static and dynamic/compression cultures for thick isotropic and anisotropic cardiac patches.
Figure 34D:
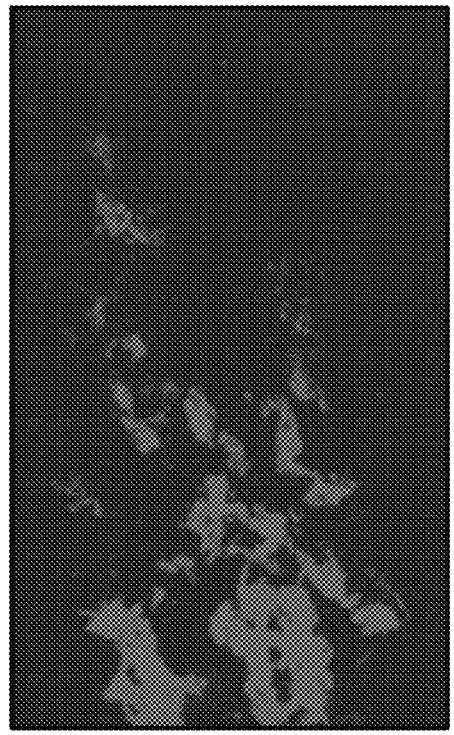
Figure 34A:
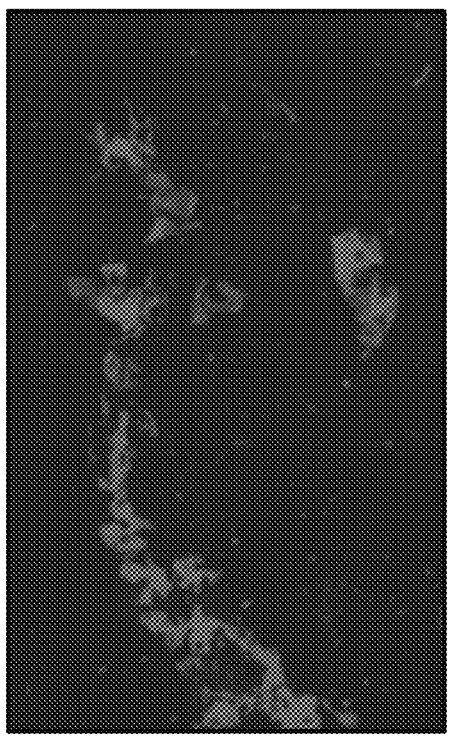
Figure 34C:
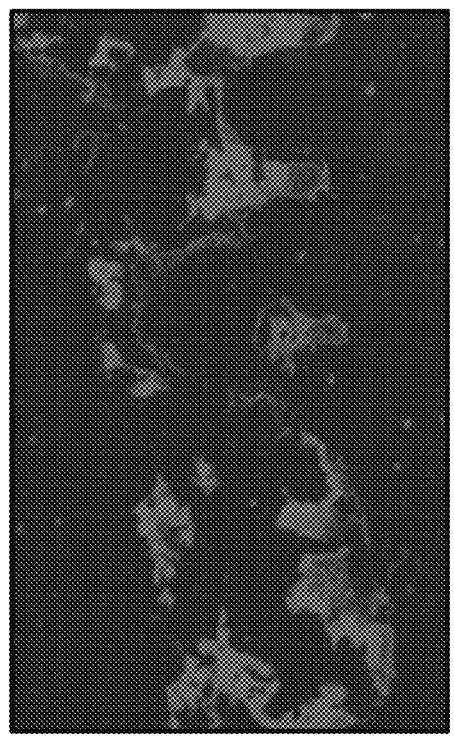
Figure 35A:
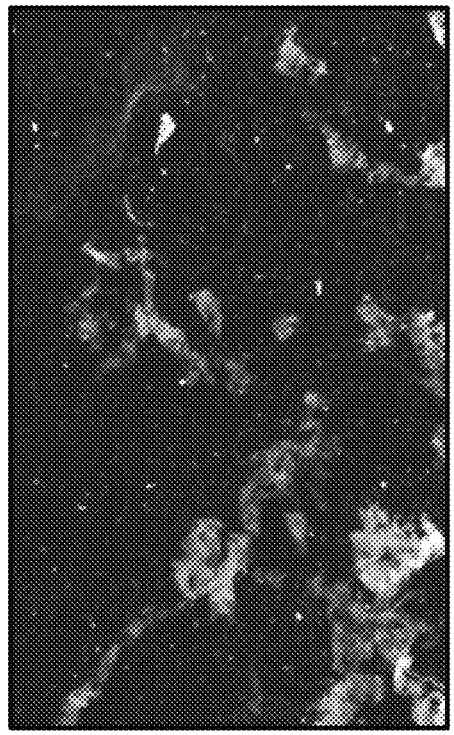
FIGS. 35A-35D illustrate H&E and immunostaining for static and dynamic/compression cultures for thick isotropic and anisotropic cardiac patches.
Figure 35B:
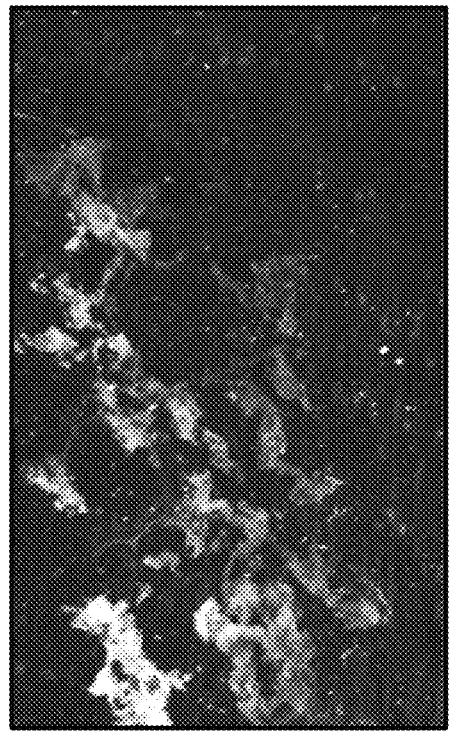
Figure 35C:
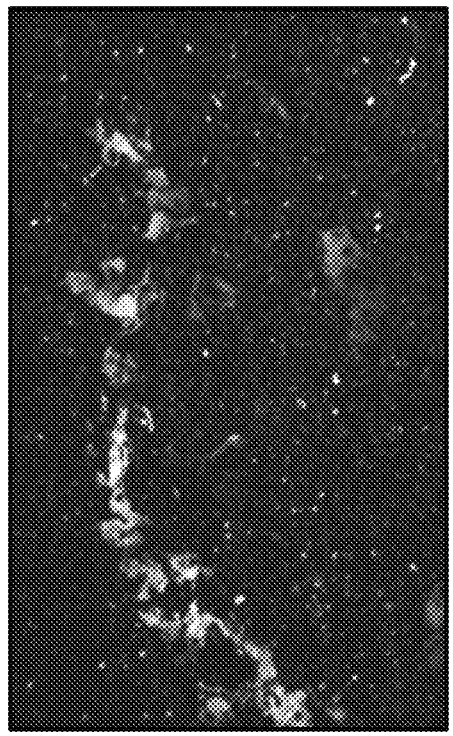
Figure 35D:
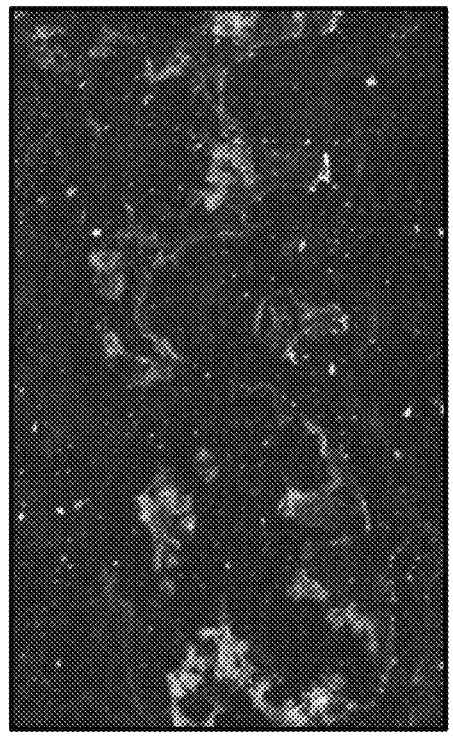
Figure 36A:
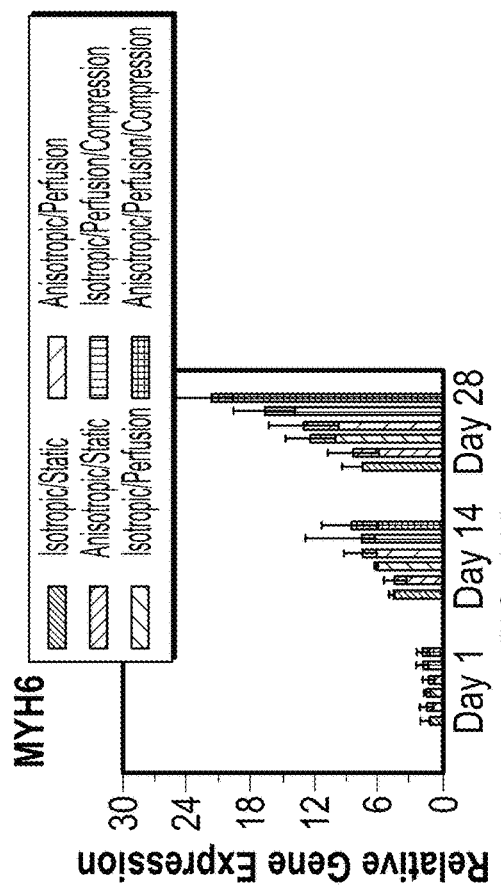
FIGS. 36A-36D is a chart having data for a gene expression analysis conducted for static, perfusion culture and under compression for thick isotropic and anisotropic constructs.
Figure 36B:
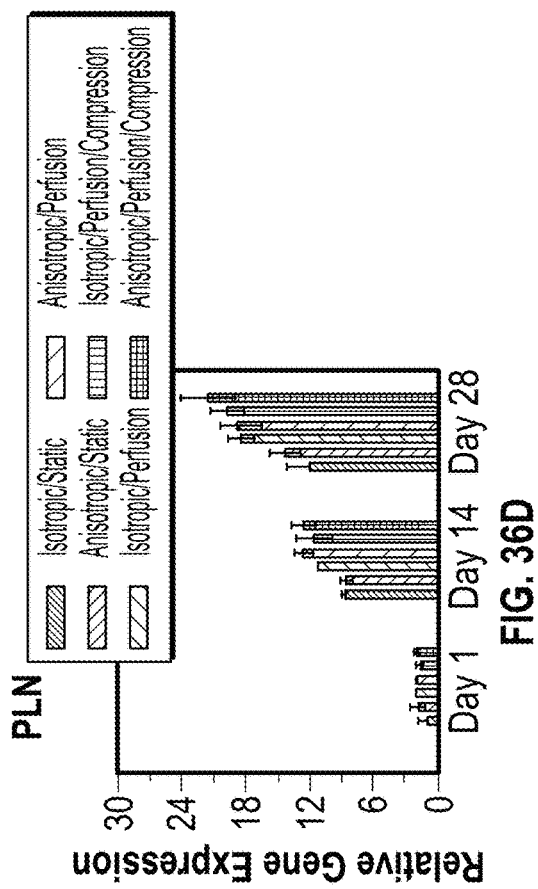
Figure 36C:
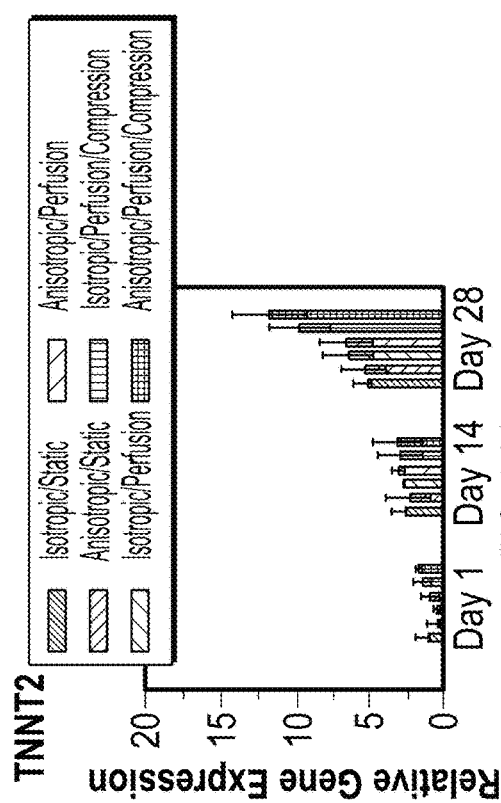
Figure 36D:
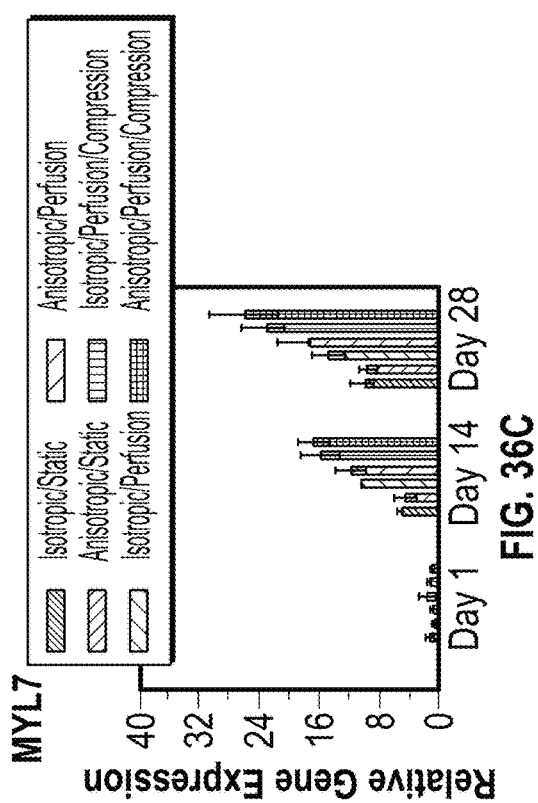
Figure 37A:
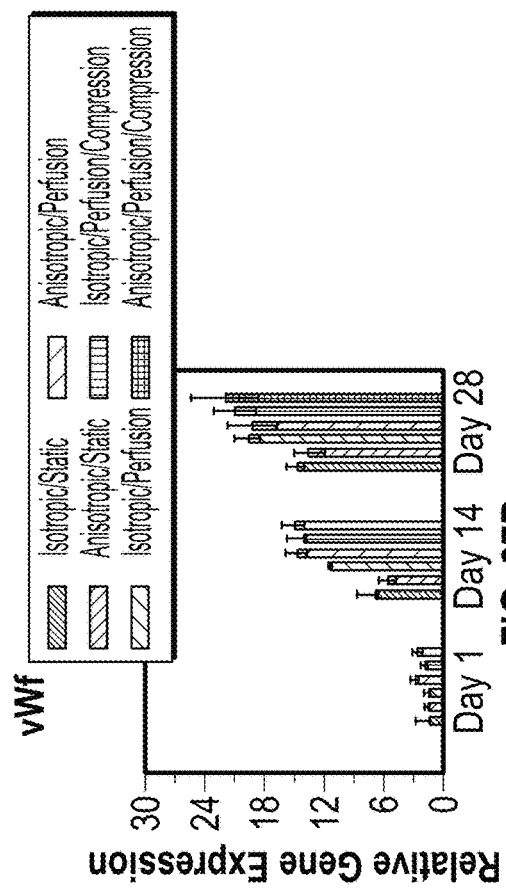
FIGS. 37A-37D is a chart having data for a gene expression analysis conducted for static, perfusion culture and under compression for thick isotropic and anisotropic constructs.
Figure 37B:
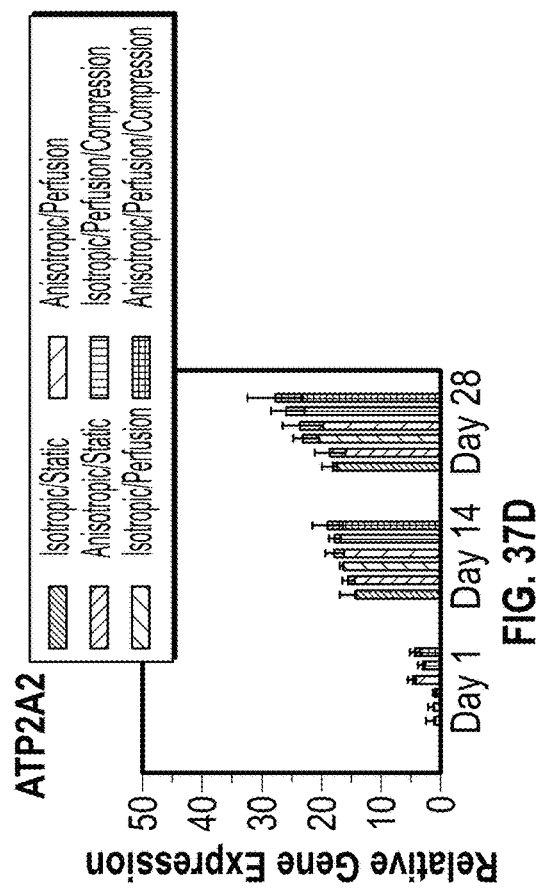
Figure 37C:
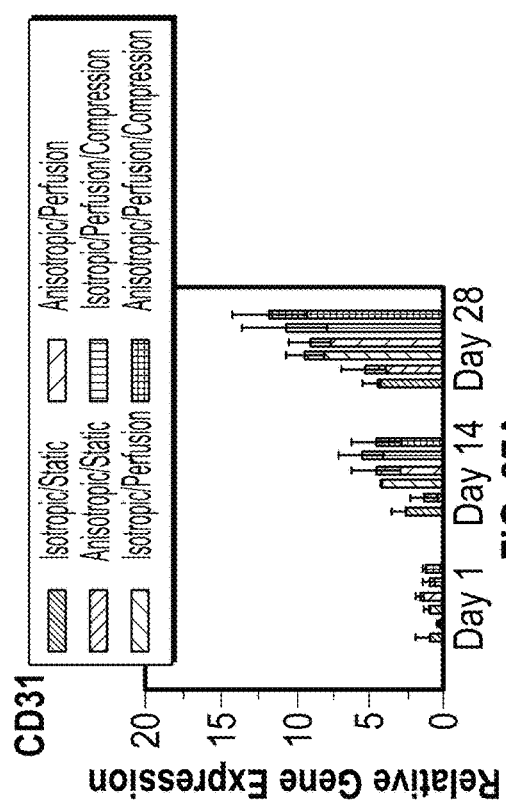
Figure 37D:
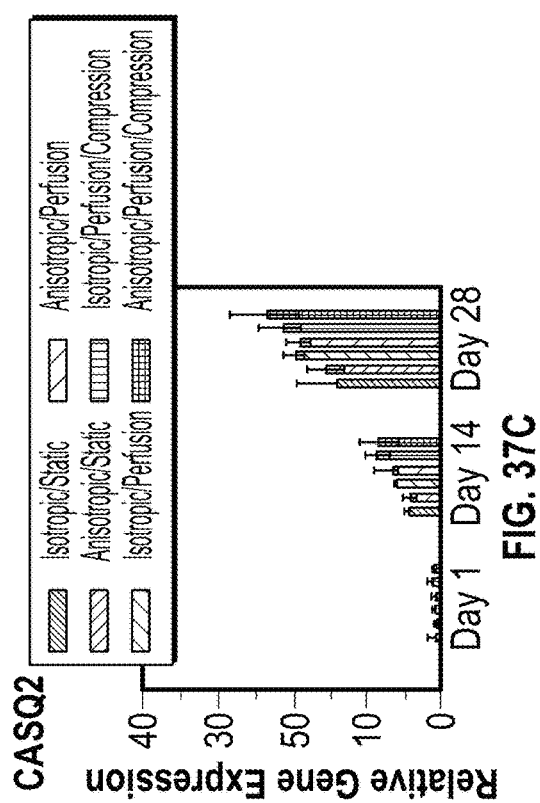

FIGS. 33A and 33C show H&E and immunostaining for static and dynamic/compression cultures for a thick isotropic patch with perfusable vessels, respectively. FIGS. 33B and 33D show immunostaining for static and dynamic/compression cultures for a thick anisotropic patch with perfusable vessels, respectively. FIGS. 34A and 34C show DAPI staining for static and dynamic/compression cultures for a thick isotropic patch with perfusable vessels, respectively. FIGS. 34B and 34D show DAPI for static and dynamic/compression cultures for a thick anisotropic patch with perfusable vessels, respectively.

FIGS. 34A and 34C show H&E and immunostaining staining for static and dynamic/compression cultures for a thick isotropic patch with perfusable vessels, respectively. FIGS. 34B and 34D show H&E and immunostaining for static and dynamic/compression cultures for a thick anisotropic patch with perfusable vessels, respectively. FIGS. 35A-35D illustrate H&E and immunostaining for static and dynamic/compression cultures for thick isotropic and anisotropic cardiac patches.

In FIGS. 36A-36D and 37A-37D a gene expression analysis was conducted for static, perfusion culture and under compression for both isotropic and anisotropic constructs. The cardiac tissue related genes including CD31 in FIG. 37A, MYH6 in FIG. 36B, MYL7 in FIG. 36C, PLN in FIG. 36D, vWF in FIG. 37B, CASQ2 in FIG. FIG. 37C, ATP2A2 in FIG. 37D.

Although a variety of information was used to explain aspects within the scope of the appended claims, no limitation of the claims should be implied based on particular features or arrangements, as one of ordinary skill would be able to derive a wide variety of implementations. Further and although some subject matter may have been described in language specific to structural features and/or method steps, it is to be understood that the subject matter defined in the appended claims is not necessarily limited to these described features or acts. Such functionality can be distributed differently or performed in components other than those identified herein. Rather, the described features and steps are disclosed as possible components of systems and methods within the scope of the appended claims.

The invention claimed is:

1. A cardiac patch for treatment of a damaged mammalian heart comprising:
   perfusable vessels embedded integratedly between hydrogel layers comprising anisotropically oriented myocardial fibers,
      wherein the walls of the perfusable vessels comprise endothelial cells, and
      wherein the cardiac patch has a thickness of at least 0.5 cm and demonstrates one or more biomimetic characteristics.

2. The cardiac patch of claim 1, wherein the one or more biomimetic characteristics comprise cardiac contraction, cardiac metabolism, cardiac tissue regeneration, cardiac physical support, or any combination thereof.

3. The cardiac patch of claim 1, wherein the perfusable vessels have a cell nutrient containing medium perfusing therein.

4. The cardiac patch of claim 1 having a thickness of at least 1 cm.

5. The cardiac patch of claim 1, wherein the anisotropically oriented myocardial fibers are laden with mammalian cells.

6. The cardiac patch of claim 1, wherein the anisotropically oriented myocardial fibers comprise stem cell-derived cardiomyocytes.

7. The cardiac patch of claim 1, wherein the perfusable vessels are formed via extrusion 3D printing.

8. The cardiac patch of claim 7, wherein the extrusion 3D printing of the perfusable vessels comprises printing with a fugitive bioink.

9. The cardiac patch of claim 8, wherein the fugitive bioink further comprises endothelial cells.

10. The cardiac patch of claim 1, wherein the anisotropically oriented myocardial fibers are formed via stereolithography 3D printing.

11. The cardiac patch of claim 10, wherein stereolithography 3D printing comprises printing with a mixed bioink having gelatin methacrylate (GelMA) and polyethylene glycol diacrylate (PEGDA).

12. The cardiac patch of claim 11, wherein the mixed bioink comprises stem-cell derived cardiomyocyte (iPS-CMs).

13. The cardiac patch of claim 1, wherein the anisotropically oriented myocardial fibers are formed in layers, and wherein the perfusable vessels are formed after at least every 5th layer of the anisotropically oriented myocardial fibers.

14. A method for treating a damaged mammalian heart, the method comprising:
   applying to the damaged heart of a mammalian subject the cardiac patch of claim 1.

15. A method for making the cardiac patch for treatment of a damaged mammalian heart of claim 1, the method comprising:
   printing a plurality of bioink layers laden with cardiomyocytes using stereolithography 3D printing to form anisotropically oriented myocardial fibers; and
   printing a fugitive ink integratedly between one or more of the plurality of layers of the anisotropically oriented myocardial fibers to form perfusable vessels.

16. The method of claim 15, further comprising removing the fugitive ink thereby leaving the perfusable vessels.

17. The method of claim 15, wherein the fugitive ink further comprises endothelial cells.

18. The method of claim 15, wherein the bioink layers comprise gelatin methacrylate (GelMA) and polyethylene glycol diacrylate (PEGDA).

19. The method of claim 15, wherein the anisotropically oriented myocardial fibers are printed in a polygonal pattern.

20. The method of claim 15, further comprising delivering a nutrient medium within the perfusable vessels.

21. The method of claim 15, wherein the cardiac patch has a thickness of at least 1 CM.

22. A system comprising:
- hydrogel layers comprising an anisotropically oriented myocardial fiber structure having perfusable vessels embedded integratedly therein,
  - wherein the walls of the perfusable vessels comprise endothelial cells,
  - wherein the anisotropically oriented myocardial fiber structure and perfusable vessels are formed via 3D bioprinting,
  - wherein the 3D bioprinting of the anisotropically oriented myocardial fiber structure comprises stereolithography, and
  - wherein the 3D bioprinting of the perfusable vessels comprises extrusion printing, and
- one or more bioinks used in the 3D bioprinting.

\* \* \* \* \*